United States Patent [19]

Grunberger et al.

[11] Patent Number: 5,591,773
[45] Date of Patent: Jan. 7, 1997

[54] INHIBITION OF CATARACT FORMATION, DISEASES RESULTING FROM OXIDATIVE STRESS, AND HIV REPLICATION BY CAFFEIC ACID ESTERS

[75] Inventors: Dezider Grunberger, Teaneck, N.J.; Krystyna Frenkel, Woodmere, N.Y.

[73] Assignees: The Trustees of Columbia University in the City of New York; New York University, both of New York, N.Y.

[21] Appl. No.: 212,569

[22] Filed: Mar. 14, 1994

[51] Int. Cl.$^6$ ............................................. A61K 31/235
[52] U.S. Cl. ................................. 514/532; 514/912
[58] Field of Search ................................. 514/532, 912

[56] References Cited

U.S. PATENT DOCUMENTS 5,008,441 4/1991 Nakanishi et al. ..................... 560/75

OTHER PUBLICATIONS

Medline Abstract of Cancer Research, Mar. 15, 1993 Frenkel et al.

Agarawl, R., et al. Inhibition of Skin Tumor Promoter--caused Induction of Epidermal Ornithine Decarboxylase in SENCAR Mice by Polyphenolic Fraction Isolated From Green Tea and Its Individual Epicatechin Derivatives. Cancer Res. (1992) 52: 3582–3588.

Babizhayev, M. A. Accumulation of Lipid Peroxidation Products in Human Cataracts. Acta Ophthalmologica (1989) 67: 281–287.

Bhuyan, K. C., et al. Lipid Peroxidation in Cataract of the Human Life Sciences. (1986) 38: 1463–1471.

Frenkel, K. Carcinogen–Mediated Oxidant Formation and Oxidative DNA Damage. Pharmac. Ther. (1992) 53: 127–166.

Frenkel, K., et al. (abstract) Inhibition of Tumor Promoter--Mediated Oxidative Processes By Caffeic Acid Phenethyl Ester (CAPE). Proc. Amer. Assoc. Cancer Res. (1992) 33: 161.

Grunberger, D., et al. Preferential Cytotoxicity on Tumor Cells by Caffeic Acid Phenethyl Ester Isolated From Propolis. Experientia (Basel) (1988) 44: 230–232.

Huang, M. T., et al. Inhibitory Effect of Curcumin. Chlorogenic Acid. Caffeic Acid, and Ferulic Acid on Tumor Promotion in Mouse Skin by 12-0-Tetradecanoylphorbol–13–Acetate. Cancer Res. (1988) 48: 5941–5946.

Rao, C. V., et al. Effect of Caffeic Acid Esters on Carcinogen–induced Mutagenicity and Human Colon Adenocarcinoma Cell Growth. Chem.–Biol. Interactions (1992) 84: 277–290.

Smart, R. C., et al. Inhibition of 12–O–Tetradecanoylphorbol–13–Acetate Induction of Ornithine Decarboxylase Activity, DNA Synthesis, and Tumor Promotion in Mouse Skin by Ascorbic Acid and Ascorbyl Palmitte. Cancer Res. (1987) 47: 6633–6638.

Wei, H., et al. In Vivo Formation of Oxidized DNA Bases in Tumor Promoter–treated Mouse Skin. Cancer Res. (1991) 51: 4443–4449.

Wei. H., et al. Suppression of Tumor Promoter–induced Oxidative Events and DNA Damage in vivo by Sarcophytol A: A possible mechanism of antipromotion. Cancer Res. (1992) 52: 2298–2303.

*Primary Examiner*—Zohreh Fay
*Attorney, Agent, or Firm*—John P. White

[57] ABSTRACT

A method of inhibiting the formation of a cataract in an eye by contacting the eye with a compound having the structure:

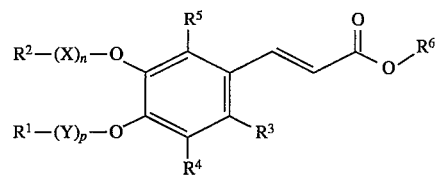

is described. Also described is a method of inhibiting the progression of cataract formation in an eye. Methods comprising administering a pharmaceutical composition comprising the above compound to inhibit the formation of a cataract in the eye of a subject and to inhibit progression of cataract formation in the eye of a subject are also described. The above compound also prevents diseases resulting from oxidative stress, including diseases comprising tumor formation resulting from oxidative stress, and also inhibits the progression of diseases resulting from oxidative stress. The above compound may furthermore be used to treat an HIV infection when combined in a pharmaceutical composition with a substance which inhibits HIV replication.

30 Claims, 13 Drawing Sheets

INHIBITION OF CATARACT FORMATION, DISEASES RESULTING FROM OXIDATIVE STRESS, AND HIV REPLICATION BY CAFFEIC ACID ESTERS

The invention disclosed herein was made with support from the U.S. Federal Government under NIH Grant No. CA37858. Accordingly, the U.S. Government has certain rights in this invention.

BACKGROUND OF THE INVENTION

Throughout this application various publications are referenced by arabic numerals within parentheses. Full citations for these publications may be found at the end of this application, preceding the claims. The disclosures of these publications in their entireties are hereby incorporated by reference into this application in order to more fully describe the state of the art to which this invention pertains. Some material incorporated into this application has previously been published by the inventors (76).

Caffeic acid phenethyl ester, hereinafter CAPE, (FIG. 1), an agent originally isolated from propolis, a product of honeybee hives, is selectively toxic to transformed cells but not to normal cells (1). More recently, CAPE was found to inhibit the transformation mediated by adenovirus type 5 E1A, as well as the expression of the transformed phenotype in Fischer cloned rat embryo fibroblasts (2). CAPE also was more cytotoxic to transformed Fischer cloned rat embryo fibroblasts than to wild type cells. The growth of other cell lines (NIH 10T½, Ltk⁻ and rat 6 cells) transformed with T24 oncogene was inhibited by CAPE, but not that of the untransformed rat 6 cells (1,2). Propolis has been considered and used in folk medicine as an anti-inflammatory agent with antitumor activity (1). One of the earlier identified propolis components that possessed anti-inflammatory and bacteriocidal properties was caffeic acid, but CAPE, which is its phenethyl ester, is more effective. The greater activity of the ester is perhaps due to its ability to more easily pass through the cell membranes. It is not known whether the free acid or its ester is the one that is active in vivo.

Reactive oxygen species (ROS), such as superoxide, $H_2O_2$, and hydroxyl radicals, can be generated during aerobic cellular metabolism (3). In addition to their significant contribution to mutagenesis, carcinogenesis, and tumor promotion (3, 4), reactive oxygen species have been implicated in the etiology and pathophysiology of many human disease, including rheumatoid arthritis, systemic lupus erythematosus, sickle cell anemia, and various forms of cancer (3, 5, 6). Reactive oxygen species induce strand breaks in DNA and oxidative modification of DNA bases, which are implicated in the mutagenic and carcinogenic effects of reactive oxygen species (3, 7–9). Although the oxidized bases can be repaired by DNA glycosylases and/or endonucleases (10–15), when the repair is not complete or timely, deleterious effects may take place. 5-hydroxymethyl-2'-deoxyuridine (HMdUrd) is cytotoxic and cytostatic to a number of mammalian cells and is mutagenic, while 8-hydroxyl-2'-deoxyguanosine (8-OHdGua) can serve as a mispairing lesion during cellular DNA replication (9, 15–17). 8-OHd-Gua has been widely used as an important biological marker for carcinogenesis and cellular oxidative stress (3, 18, 19).

It has recently been shown that the phorbol ester-type tumor promoters (12-O-tetradecanoylphorbol-13-acetate, hereinafter TPA) induce $H_2O_2$ production in mouse skin as well as cause oxidation of DNA bases in vivo (20–22). In addition, it has been found that agents possessing anti-tumor-promoting properties in vivo, also suppress inflammatory processes. Processes suppressed by such agents include infiltration of polymorphonuclear leukocytes (hereinafter PMNs), reactive oxygen species production, and oxidation of DNA bases (20–22), as well as induction of ornithine decarboxylase (ODC) and edema (23–26). A number of known anti-tumor promoters that possess all or some of those properties have been isolated from biological sources, and include sarcophytol A (isolate from marine soft coral) (27, 28), (–)-epigallocatechin gallate (EGCG, a polyphenol from green tea) (26, 29, 30), curcumin (a spice) (24, 25), and caffeic acid (24, 25).

TPA has been found to induce oxidative stress in bovine eye lens and also causes its opacity (31). Some of the chemopreventive agents (EGCG and sarcophytol A) used in tumor promotion studies were also effective inhibitors of TPA-mediated lens opacification and $H_2O_2$ production (31).

$H_2O_2$ and oxygen free radicals participate in cellular aging in humans. Cataract formation in humans is primarily associated with advanced age (32, 33, 34). Indeed, cataract development is one disease thought to be triggered by this kind of oxidative stress (34, 35, 39). In fully developed cataracts in humans and in several experimental cataract models, the oxidation of proteins (40, 41) and the peroxidation of lipids in lens tissue appears to be initiated by reactive oxygen species (33, 41–43).

As life expectancy increases, the burden of cataract formation in humans in terms of suffering and cost increases. Worldwide, cataracts are the leading cause of blindness. About 50% of individuals in the United States over 65 years of age have some stage of cataract development and about 1.3 million surgical cataract procedures are performed annually (Paton and Craig, 1990). At present, there is no proven non-surgical modality to cure cataracts, nor to retard the development of any form of cataract regardless of age.

Since the mechanism of the action of CAPE is not known, we set out to establish whether it possesses some of the properties that are common to a number of chemopreventive agents (3). Such properties include inhibition of ROS production and oxidative damage to cellular macromolecules, as well as edema and ornithine decarboxylase (ODC) induction, which are thought to contribute to tumor promotion and/or progression (3, 20–30, 44–47). Furthermore, we decided to establish whether CAPE prevents TPA-mediated ROS generation by the lens, as well as lens opacity, properties that would be useful in the prevention of cataracts (39). We tested the therapeutic use of CAPE to mitigate and delay the progression of cataracts in intact animals.

The human immunodeficiency virus enzyme HIV integrase mediates the integration of the HIV DNA into the genome of a host. It has been shown that CAPE inhibits HIV integrase (48). By combining CAPE with a substance which inhibits an HIV enzyme other than HIV integrase, HIV may be blocked at two different replication stages. We disclose herein a pharmaceutical composition comprising CAPE and a substance which inhibits HIV replication, the pharmaceutical composition being useful for treating HIV infections.

SUMMARY OF THE INVENTION

This invention provides a method of inhibiting the formation of a cataract in an eye, which comprises contacting the eye with an effective cataract-inhibiting amount of a compound having the structure:

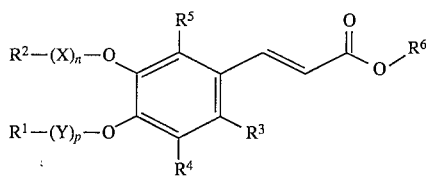

wherein
- X and Y are independently carbonyl, C=S, S=O, or O=S=O; n and p are independently 0 or 1;
- $R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^8$ are independently $C_1$–$C_6$ linear or branched alkyl;
- $R^3$, $R^4$, and $R^5$ are independently hydrogen, halogen, including F, Cl, Br, and I, trihalomethyl, linear or branched alkyl, alkenyl, alkynyl, haloalkyl, alkoxy, alkoxyalkyl, alkylthio, or (C=O) $R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$ and $R^{17}$ are independently $C_1$–$C_{18}$ linear or branched alkyl, alkenyl, or alkynyl; and
- $R^6$ is aryl or $C_1$–$C_{18}$ branched or linear alkyl, alkenyl, or alkynyl, either unsubstituted or substituted with halogen, including, F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl; or a pharmaceutically acceptable salt thereof.

This invention also provides a method of inhibiting the formation of a cataract in an eye of a subject which comprises administering to the subject a pharmaceutical composition which comprises a pharmaceutically acceptable carrier and an effective cataract-inhibiting amount of a compound having the structure:

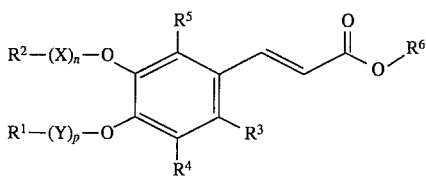

wherein
- X and Y are independently carbonyl, C=S, S=O, or O=S=O; n and p are independently 0 or 1;
- $R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$;
- wherein $R^7$ and $R^8$ are independently $C_1$–$C_6$ linear or branched alkyl;
- $R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and
- $R^6$ is aryl or $C_1$–$C_{18}$ branched or linear alkyl, alkenyl, or alkynyl, either unsubstituted or substituted with halogen, including, F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

This invention also provides a method of inhibiting the progression of cataract formation in an eye which comprises contacting the eye with an effective cataract-inhibiting amount of a compound having the structure:

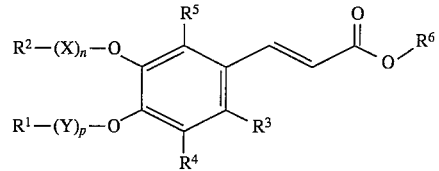

wherein
- X and Y are independently carbonyl, C=S, S=O, or O=S=O; n and p are independently 0 or 1;
- $R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^8$ are independently $C_1$–$C_6$ linear or branched alkyl;
- $R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and
- $R^6$ is aryl or $C_1$–$C_{18}$ branched or linear alkyl, alkenyl, or alkynyl, either unsubstituted or substituted with halogen, including, F, Cl, Br, and I, $C_1$–$C_6$ alkoxy, (C=O)$R^{18}$, (C=O)O$R^{19}$, or aryl; wherein
- $R^{18}$ and $R^{19}$ are independently $C_1$–$C_6$ branched or linear alkyl;

or a pharmaceutically acceptable salt thereof.

This invention also provides a method of inhibiting the progression of cataract formation in an eye of a subject which comprises administering to the subject a pharmaceutical composition which comprises a pharmaceutically acceptable carrier and an effective cataract-inhibiting amount of a compound having the structure:

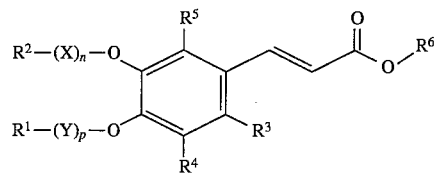

wherein
- X and Y are independently carbonyl, C=S, S=O, or O=S=O; n and p are independently 0 or 1;
- $R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$;
- wherein $R^7$ and $R^8$ are independently $C_1$–$C_6$ linear or branched alkyl;
- $R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)R$^9$, (C=O)OR$^{10}$, O(C=O)R$^{11}$, (C=S)R$^{12}$, (C=S)OR$^{13}$, O(C=S)R$^{14}$, (S=O)R$^{15}$, (S=O)OR$^{16}$, or (O=S=O)OR$^{17}$; wherein R$^9$, R$^{10}$, R$^{11}$, R$^{12}$, R$^{13}$, R$^{14}$, R$^{15}$, R$^{16}$, and R$^{17}$ are independently C$_1$–C$_{18}$ linear or branched alkyl, alkenyl, or alkynyl; and R$^6$ is aryl or C$_1$–C$_{18}$ branched or linear alkyl, alkenyl, or alkynyl, either unsubstituted or substituted with halogen, including, F, Cl, Br, and I, C$_1$–C$_6$ alkoxy, (C=O)R$^{18}$, (C=O)OR$^{19}$, or aryl; wherein R$^{18}$ and R$^{19}$ are independently C$_1$–C$_6$ branched or linear alkyl; or a pharmaceutically acceptable salt thereof.

This invention also provides a method of preventing in a subject a disease resulting from oxidative stress which comprises administering to the subject a pharmaceutical composition comprising a pharmaceutically acceptable carrier and an effective oxidative stress-inhibiting amount of a compound having the structure:

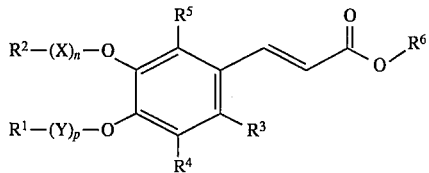

wherein

X and Y are independently carbonyl, C=S, S=O, or O=S=O; n and p are independently 0 or 1;

R$^1$ and R$^2$ are independently hydrogen, linear or branched C$_1$–C$_{18}$ alkyl, alkenyl, or alkynyl, either unsubstituted or substituted with halogen, including F, Cl, Br, and I, C$_1$–C$_6$ alkoxy, (C=O)R$^7$, or (C=O)OR$^8$; wherein R$^7$ and R$^8$ are independently C$_1$–C$_6$ linear or branched alkyl;

R$^3$, R$^4$, and R$^5$ are independently hydrogen, halogen, including F, Cl, Br, and I, trihalomethyl, C$_1$–C$_{18}$ linear or branched alkyl, alkenyl, alkynyl, haloalkyl, alkoxy, alkoxyalkyl, alkylthio, or (C=O) R$^9$, (C=O)OR$^{10}$, O(C=O)R$^{11}$, (C=S)R$^{12}$, (C=S)OR$^{13}$, O(C=S)R$^{14}$, (S=O)R$^{15}$, (S=O)OR$^{16}$, or (O=S=O)OR$^{17}$; wherein R$^9$, R$^{10}$, R$^{11}$, R$^{12}$, R$^{13}$, R$^{14}$, R$^{15}$, R$^{16}$, and R$^{17}$ are independently C$_1$–C$_{18}$ linear or branched alkyl, alkenyl, or alkynyl; and R$^6$ is aryl or C$_1$–C$_{18}$ branched or linear alkyl, alkenyl, or alkynyl, either unsubstituted or substituted with halogen, including, F, Cl, Br, and I, C$_1$–C$_6$ alkoxy, (C=O)R$^{18}$, (C=O)OR$^{19}$, or aryl; wherein R$^{18}$ and R$^{19}$ are independently C$_1$–C$_6$ branched or linear alkyl; or a pharmaceutically acceptable salt thereof.

This invention also provides a method of inhibiting in a subject the progression of a disease resulting from oxidative stress which comprises administering to the subject a pharmaceutical composition comprising a pharmaceutically acceptable carrier and an effective oxidative stress-inhibiting amount of a compound having the structure:

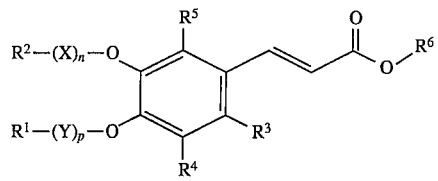

wherein

X and Y are independently carbonyl, C=S, S=O, or O=S=O; n and p are independently 0 or 1;

R$^1$ and R$^2$ are independently hydrogen, linear or branched C$_1$–C$_{18}$ alkyl, alkenyl, or alkynyl, either unsubstituted or substituted with halogen, including F, Cl, Br, and I, C$_1$–C$_6$ alkoxy, (C=O)R$^7$, or (C=O)OR$^8$; wherein R$^7$ and R$^8$ are independently C$_1$–C$_6$ linear or branched alkyl;

R$^3$, R$^4$, and R$^5$ are independently hydrogen, halogen, including F, Cl, Br, and I, trihalomethyl, C$_1$–C$_{18}$ linear or branched alkyl, alkenyl, alkynyl, haloalkyl, alkoxy, alkoxyalkyl, alkylthio, or (C=O)R$^9$, (C=O)OR$^{10}$, O(C=O)R$^{11}$, (C=S)R$^{12}$, (C=S)OR$^{13}$, O(C=S)R$^{14}$, (S=O)R$^{15}$, (S=O)OR$^{16}$, or (O=S=O)OR$^{17}$; wherein R$^9$, R$^{10}$, R$^{11}$, R$^{12}$, R$^{13}$, R$^{14}$, R$^{15}$, R$^{16}$, and R$^{17}$ are independently C$_1$–C$_{18}$ linear or branched alkyl, alkenyl, or alkynyl; and R$^6$ is aryl or C$_1$–C$_{18}$ branched or linear alkyl, alkenyl, or alkynyl, either unsubstituted or substituted with halogen, including, F, Cl, Br, and I; C$_1$–C$_6$ alkoxy, (C=O)R$^{18}$, (C=O)OR$^{19}$, or aryl; wherein R$^{18}$ and R$^{19}$ are independently C$_1$–C$_6$ branched or linear alkyl; or a pharmaceutically acceptable salt thereof.

This invention also provides a method of treating a subject having an HIV infection which comprises administering to the subject a pharmaceutical composition comprising a pharmaceutically acceptable carrier, a substance which inhibits HIV replication, and an effective HIV integrase-inhibiting amount of a compound having the structure:

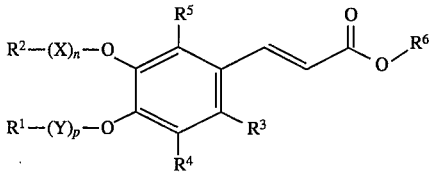

wherein

X and Y are independently carbonyl, C=S, S=O, or O=S=O; n and p are independently 0 or 1;

R$^1$ and R$^2$ are independently hydrogen, linear or branched C$_1$–C$_{18}$ alkyl, alkenyl, or alkynyl, either unsubstituted or substituted with halogen, including F, Cl, Br, and I, C$_1$–C$_6$ alkoxy, (C=O)R$^7$, or (C=O)OR$^8$; wherein R$^7$ and R$^8$ are independently C$_1$–C$_6$ linear or branched alkyl;

R$^3$, R$^4$, and R$^5$ are independently hydrogen, halogen, including F, Cl, Br, and I, trihalomethyl, C$_1$–C$_{18}$ linear or branched alkyl, alkenyl, alkynyl, haloalkyl, alkoxy, alkoxyalkyl, alkylthio, or (C=O)R$^9$, (C=O)OR$^{10}$, O(C=O)R$^{11}$, (C=S)R$^{12}$, (C=S)OR$^{13}$, O(C=S)R$^{14}$, (S=O)R$^{15}$, (S=O)OR$^{16}$, or (O=S=O)OR$^{17}$; wherein R$^9$, R$^{10}$, R$^{11}$, R$^{12}$, R$^{13}$, R$^{14}$, R$^{15}$, R$^{16}$, and R$^{17}$ are independently C$_1$–C$_{18}$ linear or branched alkyl, alkenyl, or alkynyl; and R$^6$ is aryl or C$_1$–C$_{18}$ branched or linear alkyl, alkenyl, or alkynyl, either unsubstituted or substituted with halogen, including, F, Cl, Br, and I, $C_1$–$C_6$ alkoxy (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

Finally, this invention provides a pharmaceutical composition for treating an HIV infection in a subject which comprises a pharmaceutically acceptable carrier, a substance which inhibits HIV replication, and an effective HIV integrase-inhibiting amount of a compound having the structure:

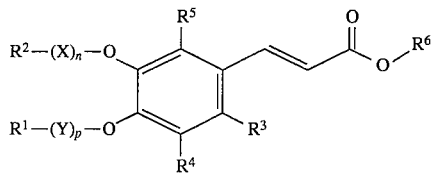

wherein

X and Y are independently carbonyl, C=S, S=O, or O=S=O; n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^8$ are independently $C_1$–$C_6$ linear or branched alkyl;

$R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, including, F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

BRIEF DESCRIPTION OF THE FIGURES

FIGS. 2A–2D. CAPE-mediated inhibition of TPA-induced oxidative processes in SENCAR mice. Mice were topically treated with 6.5 nmol CAPE 30 min prior to 6.5 nmol TPA, and this regimen was repeated 20 h later. Mice were sacrificed 1 h after the last treatment and the skin removed for determination of: (FIG. 2A) PMN infiltration (by measuring myeloperoxidase (MPO)); (FIG. 2B) $H_2O_2$; (FIG. 2C) HMdUrd (HMdU); and (FIG. 2D) 8-OHdGua (8-OHdG), according to procedures described in the "Experimental Details" Section, infra. □, controls treated with acetone in place of CAPE and TPA; ■, treatment with acetone followed by TPA; ■, treatment with CAPE followed by TPA. Results are expressed as mean ± SE (bars) from two experiments (2 mice/experiment) in the CAPE series. Data for acetone (ACT)- and TPA-treated mean values were collected from over 20 experiments.

DETAILED DESCRIPTION OF THE INVENTION

Figure 1:
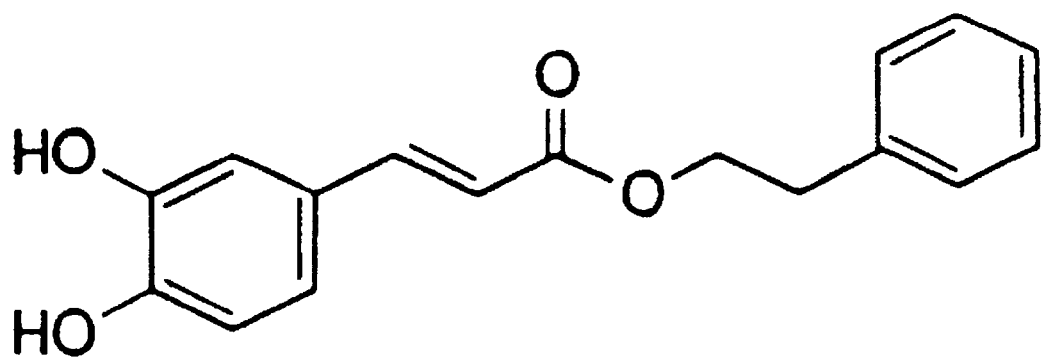
FIG. 1. Structure of caffeic acid phenethyl ester (CAPE).

This invention provides a method of inhibiting the formation of a cataract in an eye, which comprises contacting the eye with an effective cataract-inhibiting amount of a compound having the structure:

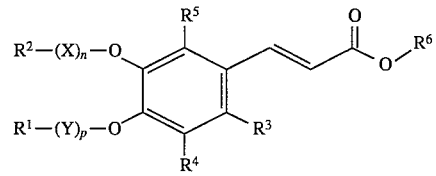

wherein

X and Y are independently carbonyl, C=S, S=O, or O=S=O; n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^8$ are independently $C_1$–$C_6$ linear or branched alkyl;

$R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S) $R^{14}$, (S=O) $R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, including, F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl; or a pharmaceutically acceptable salt thereof.

As used herein, the phrase "halo" in the terms "haloalkyl" and "trihalomethyl" is intended to mean F, Cl, Br, or I.

Methods of synthesizing caffeic acid esters which may be used to synthesize compounds having the above-defined structure have been disclosed in Nakanishi et al., U.S. Pat. No. 5,008,441, the disclosure of which is hereby incorporated by reference. Further examples of the above-defined compound can be readily synthesized by one of ordinary skill in the art based on the disclosure of U.S. Pat. No. 5,008,441 and using techniques generally known to those of ordinary skill. Examples of such methods include the general organic synthesis techniques disclosed in such texts as March, J. *Advanced Organic Chemistry*, 3rd ed. (Wiley; New York: 1985), the contents of which are hereby incorporated by reference.

In a preferred embodiment, n and p are 0, and $R_1$, $R_2$, $R_3$, $R_4$, and $R_5$ are hydrogen. In another preferred embodiment, n and p are 0; $R_1$, $R_2$, $R_3$, $R_4$, and $R_5$ are hydrogen; and $R_6$ is hexyl, butyl, ethyl, or phenylethyl.

In a further preferred embodiment, the compound has the structure:

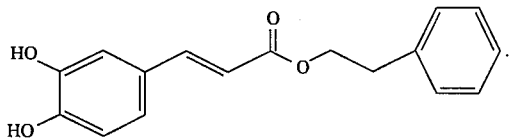

In the above-described method of inhibiting the formation of a cataract in an eye, the eye may already contain one or more developing or fully developed cataracts before it is contacted with the compound. Accordingly, the above-described method can be used to inhibit the formation of further cataracts in the eye, or to inhibit the formation of mature cataracts from the developing cataracts already present in the eye. Alternatively, the eye may be free of any developing or fully developed cataracts before it is contacted with the compound.

As used herein, the term "contacting" is intended to encompass any method of directly applying the compound to the eye. In the above-described method, any suitable means known to those of ordinary skill in the art may be used to contact the eye with the compound. Examples of such methods include, but are not limited to, the compound being injected into the eye, or being dropped or sprayed into the eye, or otherwise topically applied to the eye.

As used herein, the term "effective cataract-inhibiting amount" is intended to mean any amount which will inhibit the progression or formation of cataracts in an eye or inhibit the progression or formation of mature cataracts from any developing cataracts already present in the eye. The effective cataract-inhibiting amount of the compound will depend on various factors known to those of ordinary skill in the art. Such factors include, but are not limited to, the size of the eye, and the number and progression of any fully developed or developing cataracts already present in the eye. The effective cataract-inhibiting amount will also depend on whether the eye is to be contacted a single time with the compound or whether the eye is to be contacted with the compound periodically, over a stretch of time. The stretch of time may be any number of days, weeks, months, or years. In one embodiment, the effective cataract-inhibiting amount of the compound may be between about 1.0 μg and 20.0 μg per eye. Preferably, the effective cataract-inhibiting amount is between about 1.0 μg and 10.0 μg per eye. More preferably, the effective cataract-inhibiting amount of the compound is between about 2.0 μg and about 5.0 μg per eye, this amount being especially preferred when the eye is contacted with the compound periodically, over a stretch of time.

This invention also provides a method of inhibiting the formation of a cataract in an eye of a subject which comprises administering to the subject a pharmaceutical composition which comprises a pharmaceutically acceptable carrier and an effective cataract-inhibiting amount of a compound having the structure:

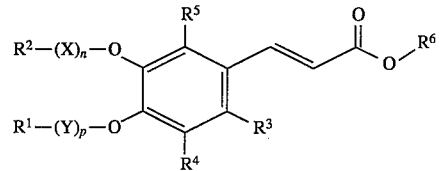

wherein

X and Y are independently carbonyl, C=S, S=O, or O=S=O; n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^a$ are independently $C_1$–$C_6$ linear or branched alkyl;

$R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, including, F, Cl, Br, and I, $C_1$–$C_6$ alkoxy (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

In a preferred embodiment, n and p are 0, and $R_1$, $R_2$, $R_3$, $R_4$, and $R_5$ are hydrogen. In another preferred embodiment, n and p are 0; $R_1$, $R_2$, $R_3$, $R_4$, and $R_5$ are hydrogen; and $R_6$ is hexyl, butyl, ethyl, or phenylethyl.

In a further preferred embodiment, the compound has the structure:

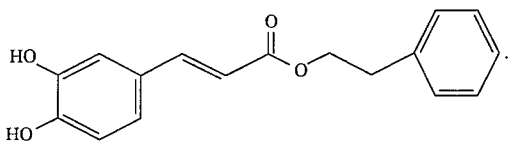

In the above-described method of inhibiting the formation of a cataract in an eye of a subject, the eye may already contain one or more developing or fully developed cataracts before the pharmaceutical composition is administered to the subject. Accordingly, the above-described method can be used to inhibit the formation of further cataracts in the eye of the subject, or to inhibit the formation of mature cataracts from the developing cataracts already present in the eye of the subject. Alternatively, the eye of the subject may be free of any developing or fully developed cataracts before the pharmaceutical composition is administered to the subject.

In the above-described method, any suitable means known to those of ordinary skill in the art may be used to administer the pharmaceutical composition to the subject. In one embodiment, administering the pharmaceutical composition to the subject comprises applying the pharmaceutical composition to the eye of the subject.

In another embodiment, the pharmaceutical composition is orally administered to the subject. If oral administration is employed, the pharmaceutical composition may be in the form of a capsule, tablet, or solution.

In another embodiment, the pharmaceutical composition is injected into the subject. Injection may be intramuscular, intraperitoneal, intravenous, or subcutaneous. The pharmaceutical composition may be injected into any part of the subject's body, including into one or both of the subject's eyes.

In a further embodiment, the pharmaceutical composition is topically applied to the subject. If the pharmaceutical composition is topically applied, the pharmaceutical composition may be in the form of a lotion or cream. The pharmaceutical composition may be topically applied to any part of the subject's body, since topical administration will result in systemic effects. If the pharmaceutical composition is topically applied to one or both of the eyes of the subject, the pharmaceutical composition may be in the form of eye drops.

Finally, the administration may comprise surgically removing the lens of the eye from the subject, applying the pharmaceutical composition to the lens, and then surgically replacing the lens.

As used herein, the term "pharmaceutically acceptable carrier" encompasses any of the standard pharmaceutically accepted carriers known to those of ordinary skill in the art. Examples of such standard carriers include, but are not limited to, phosphate buffered saline solution, water, emulsions such as oil/water emulsions or a triglyceride emulsion, various types of wetting agents, tablets, coated tablets and capsules. A suitable pharmaceutically accepted carrier may be selected taking into account the chosen mode of administration.

As used herein, the term "effective cataract-inhibiting amount" is intended to mean any amount which will inhibit the progression or formation of cataracts in an eye or inhibit the progression or formation of mature cataracts from any developing cataracts already present in the eye. The effective cataract-inhibiting amount of the compound will depend on various factors known to those of ordinary skill in the art.

Such factors include, but are not limited to, the size of the eye, the number and progression of any fully developed or developing cataracts already present in the eye, and the mode of administration. The effective cataract-inhibiting amount will also depend on whether the pharmaceutical composition is to be administered a single time, or whether the pharmaceutical composition is to be administered periodically, over a stretch of time. The stretch of time may be any number of days, weeks, months, or years. In one embodiment, the effective cataract-inhibiting amount of the compound may be between about 1.0 μg and 20.0 μg. Preferably, the effective cataract-inhibiting amount is between about 1.0 μg and 10.0 μg.

More preferably, the effective cataract-inhibiting amount of the compound is between about 2.0 μg and about 5.0 μg, this amount being especially preferred when the pharmaceutical composition is applied to one or both of the eyes of the subject, periodically, over a stretch of time.

In one embodiment of the above-described method of inhibiting the formation of a cataract in an eye of a subject, the subject is a mammal. When the subject is a mammal, the subject may be a human being.

This invention also provides a method of inhibiting the progression of cataract formation in an eye which comprises contacting the eye with an effective cataract-inhibiting amount of a compound having the structure:

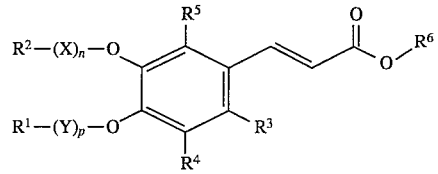

wherein

X and Y are independently carbonyl, C=S, S=O, or O=S=O; n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^8$ are independently $C_1$–$C_6$ linear or branched alkyl;

$R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, including, F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

In a preferred embodiment, n and p are 0, and $R_1$, $R_2$, $R_3$, $R_4$, and $R_5$ are hydrogen. In another preferred embodiment, n and p are 0; $R_1$, $R_2$, $R_3$, $R_4$, and $R_5$ are hydrogen; and $R_6$ is hexyl, butyl, ethyl, or phenylethyl.

In a further preferred embodiment, the compound has the structure:

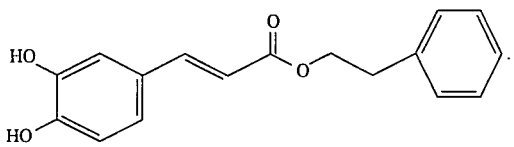

In the above-described method of inhibiting the progression of cataract formation in an eye, the eye may already contain one or more developing or fully developed cataracts before it is contacted with the compound. Accordingly, the above-described method can be used to inhibit the progression of cataract formation from any developing cataracts already present in the eye.

Alternatively, the eye may be free of any developing or fully developed cataracts.

As used herein, the term "contacting" is intended to encompass any method of directly applying the compound to the eye. In the above-described method, any suitable means known to those of ordinary skill in the art may be used to contact the eye with the compound. Examples of such methods include, but are not limited to, the compound being injected into the eye, or being dropped or sprayed into the eye, or otherwise topically applied to the eye.

As used herein, the term "effective cataract-inhibiting amount" is intended to mean any amount which will inhibit the progression or formation of cataracts in an eye or inhibit the progression or formation of mature cataracts from any developing cataracts already present in the eye. The effective cataract-inhibiting amount of the compound will depend on various factors known to those of ordinary skill in the art. Such factors include, but are not limited to, the size of the eye, and the number and progression of any fully developed or developing cataracts already present in the eye. The effective cataract-inhibiting amount will also depend on whether the eye is to be contacted a single time with the compound or whether the eye is to be contacted with the compound periodically, over a stretch of time. The stretch of time may be any number of days, weeks, months, or years. In one embodiment, the effective cataract-inhibiting amount of the compound may be between about 1.0 µg and 20.0 µg per eye. Preferably, the effective cataract-inhibiting amount is between about 1.0 µg and 10.0 µg per eye. More preferably, the effective cataract-inhibiting amount of the compound is between about 2.0 µg and about 5.0 µg per eye, this amount being especially preferred when the eye is contacted with the compound periodically, over a stretch of time.

Still further, this invention provides a method of inhibiting the progression of cataract formation in an eye of a subject which comprises administering to the subject a pharmaceutical composition which comprises a pharmaceutically acceptable carrier and an effective cataract-inhibiting amount of a compound having the structure:

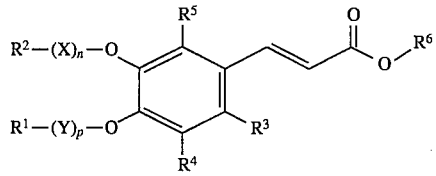

wherein

X and Y are independently carbonyl, C=S, S=O, or O=S=O; n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, (C=O)O$R^8$; wherein $R^7$ and $R^8$ are independently $C_1$–$C_6$ linear or branched alkyl;

$R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, including, F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

In a preferred embodiment, n and p are 0, and $R_1$, $R_2$, $R_3$, $R_4$, and $R_5$ are hydrogen. In another preferred embodiment, n and p are 0; $R_1$, $R_2$, $R_3$, $R_4$, and $R_5$ are hydrogen; and $R_6$ is hexyl, butyl, ethyl, or phenylethyl.

In a further preferred embodiment, the compound has the structure:

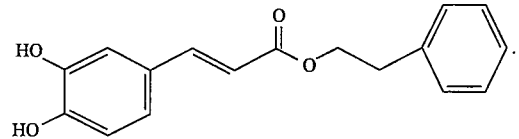

In the above-described method of inhibiting the progression of cataract formation in an eye of a subject, the eye may already contain one or more developing or fully developed cataracts before the pharmaceutical composition is administered to the subject. Accordingly, the above-described method can be used to inhibit the progression of cataract formation from any developing cataracts already present in the eye of the subject. Alternatively, the eye of the subject may be free of any developing or fully developed cataracts before the pharmaceutical composition is administered to the subject.

In the above-described method, any suitable means known to those of ordinary skill in the art may be used to administer the pharmaceutical composition to the subject. In one embodiment, administering the pharmaceutical composition to the subject comprises applying the pharmaceutical composition to the eye of the subject.

In another embodiment, the pharmaceutical composition is orally administered to the subject. If oral administration is employed, the pharmaceutical composition may be in the form of a capsule, tablet, or solution.

In another embodiment, the pharmaceutical composition is injected into the subject. Injection may be intramuscular, intraperitoneal, intravenous, or subcutaneous. The pharmaceutical composition may be injected into any part of the subject's body, including into one or both of the subject's eyes.

In a further embodiment, the pharmaceutical composition is topically applied to the subject. If the pharmaceutical composition is topically applied, the pharmaceutical composition may be in the form of a lotion or cream. The pharmaceutical composition may be topically applied to any part of the subject's body, since topical administration will result in systemic effects. If the pharmaceutical composition is topically applied to one or both of the eyes of the subject, the pharmaceutical composition may be in the form of eye drops.

Finally, the administration may comprise surgically removing the lens of the eye from the subject, applying the pharmaceutical composition to the lens, and then surgically replacing the lens.

As used herein, the term "pharmaceutically acceptable carrier" encompasses any of the standard pharmaceutically accepted carriers known to those of ordinary skill in the art. Examples of such standard carriers include, but are not limited to, phosphate buffered saline solution, water, emulsions such as oil/water emulsions or a triglyceride emulsion, various types of wetting agents, tablets, coated tablets and capsules. A suitable pharmaceutically accepted carrier may be selected taking into account the chosen mode of administration.

As used herein, the term "effective cataract-inhibiting amount" is intended to mean any amount which will inhibit the progression or formation of cataracts in an eye or inhibit the progression or formation of mature cataracts from any developing cataracts already present in the eye. The effective cataract-inhibiting amount of the compound will depend on various factors known to those of ordinary skill in the art. Such factors include, but are not limited to, the size of the eye, the number and progression of any fully developed or developing cataracts already present in the eye, and the mode of administration. The effective cataract-inhibiting amount will also depend on whether the pharmaceutical composition is to be administered a single time, or whether the pharmaceutical composition is to be administered periodically, over a stretch of time. The stretch of time may be any number of days, weeks, months, or years. In one embodiment, the effective cataract-inhibiting amount of the compound may be between about 1.0 µg and 20.0 µg per eye. Preferably, the effective cataract-inhibiting amount is between about 1.0 µg and 10.0 µg. More preferably, the effective cataract-inhibiting amount of the compound is between about 2.0 µg and about 5.0 µg, this amount being especially preferred when the pharmaceutical composition is applied to one or both of the eyes of the subject, periodically, over a stretch of time.

In one embodiment of the above-described method of inhibiting the progression of cataract formation in an eye of a subject, the subject is a mammal. When the subject is a mammal, the subject may be a human being.

This invention further provides a method of preventing in a subject a disease resulting from oxidative stress which comprises administering to the subject a pharmaceutical composition comprising a pharmaceutically acceptable carrier and an effective oxidative stress-inhibiting amount of a compound having the structure:

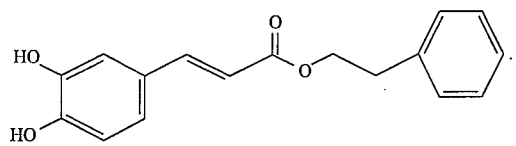

wherein

X and Y are independently carbonyl, C=S, S=O, or O=S=O; n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^8$ are independently $C_1$–$C_6$ linear or branched alkyl;

$R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, including, F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

In a preferred embodiment, n and p are 0, and $R_1$, $R_2$, $R_3$, $R_4$, and $R_5$ are hydrogen. In another preferred embodiment, n and p are 0; $R_1$, $R_2$, $R_3$, $R_4$, and $R_5$ are hydrogen; and $R_6$ is hexyl, butyl, ethyl, or phenylethyl.

In a further preferred embodiment, the compound has the structure:

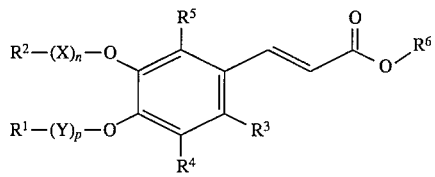

As used herein, a disease resulting from oxidative stress is any disease resulting from the effects of reactive oxygen species generated in cells. Reactive oxygen species include superoxide, $H_2O_2$, and hydroxyl radicals. Reactive oxygen species may be generated in cells during aerobic cellular metabolism. Also, certain external agents are known to result in the generation of reactive oxygen species in cells, and thereby in an increase in oxidative stress. External agents which may result in the generation of reactive oxidative species in cells include certain types of radiation, such as UV radiation or X-rays, chemotherapeutic agents, pesticides, and cigarette smoke. Metabolizing xenobiotics or fatty foods may also result in generation of reactive oxygen species in cells.

Diseases which may result from oxidative stress are known to those of ordinary skill in the art, and include, but are not limited to, rheumatoid arthritis, lupus, and sickle cell anemia. Oxidative stress causes oxidation of DNA bases and damages DNA in cells, and consequently may also lead to the formation of tumors. Thus, diseases which result from oxidative stress include diseases comprising the formation of tumors resulting from oxidative stress. Diseases which comprise the formation of tumors include cancer.

In the above-described method, any suitable means known to those of ordinary skill in the art may be used to administer the pharmaceutical composition to the subject. In one embodiment, the pharmaceutical composition is topically applied to a part of the subject's body where oxidative stress is expected. However, topical application of the pharmaceutical composition to one part of the subject's body can be expected to have beneficial systemic effects on other parts. When the composition is topically applied, it may be in the form of a cream or a lotion.

In another embodiment, the pharmaceutical composition is orally administered to the subject. If oral administration is employed, the pharmaceutical composition may be in the form of a capsule, tablet, or solution.

In another embodiment, the pharmaceutical composition may be injected into the subject. Injection may be intramuscular, intraperitoneal, intravenous, or subcutaneous. The pharmaceutical composition may be injected into any part of the subject's body, including into a part where oxidative stress is expected.

As used herein, the term "pharmaceutically acceptable carrier" encompasses any of the standard pharmaceutically accepted carriers known to those of ordinary skill in the art. Examples of such standard carriers include, but are not limited to, phosphate buffered saline solution, water, emulsions such as oil/water emulsions or a triglyceride emulsion, various types of wetting agents, tablets, coated tablets and capsules. A suitable pharmaceutically accepted carrier may be selected taking into account the chosen mode of administration.

As used herein, the term "effective oxidative stress-inhibiting amount" is meant to indicate that amount which will inhibit the generation of reactive oxygen species in cells. The effective oxidative stress-inhibiting amount of the compound will depend on various factors known to those of ordinary skill in the art. Such factors include, but are not limited to, the size of the subject and the mode of administration. The effective oxidative stress-inhibiting amount of the compound will also depend on whether the pharmaceutical composition is to be administered a single time to the subject, or whether it is to be administered periodically over a stretch of time. A stretch of time may be any number of days, weeks, months, or years. In one embodiment, the oxidative stress-inhibiting amount of the compound may be between about 0.01 µg and about 20.0 µg per dose. Preferably the oxidative stress-inhibiting amount of the compound is between about 0.01 µg and about 10.0 µg per dose. Even more preferably, the oxidative stress-inhibiting amount of the compound is between about 0.02 µg and 2.0 µg per dose, this amount being especially preferred when the pharmaceutical composition is administered periodically, over a stretch of time.

In one embodiment of the above-described method of preventing in a subject a disease resulting from oxidative stress, the subject is a mammal. When the subject is a mammal, the subject may be a human being.

Further provided is a method of inhibiting in a subject the progression of a disease resulting from oxidative stress which comprises administering to the subject a pharmaceutical composition comprising a pharmaceutically acceptable carrier and an effective oxidative stress-inhibiting amount of a compound having the structure:

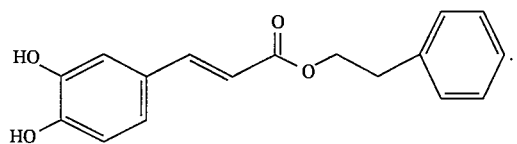

wherein

X and Y are independently carbonyl, C=S, S=O, or O=S=O; n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F Cl, Br, and I, $C_1$–$C_6$ alkoxy, (C=O)$R^7$, or, (C=O)O$R^8$; wherein $R^7$ and $R^8$ are independently $C_1$–$C_6$ linear or branched alkyl;

$R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)O$R^{12}$, (C=S)$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, including, F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

In a preferred embodiment, n and p are 0, and $R_1$, $R_2$, $R_3$, $R_4$, and $R_5$ are hydrogen. In another preferred embodiment, n and p are 0; $R_1$, $R_2$, $R_3$, $R_4$, and $R_5$ are hydrogen; and $R_6$ is hexyl, butyl, ethyl, or phenylethyl.

In further preferred embodiment, the compound has the structure:

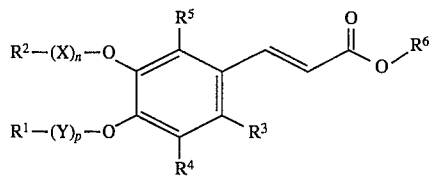

As described above, a disease resulting from oxidative stress is any disease resulting from the effects of reactive oxygen species generated in cells. By inhibiting generation of reactive oxygen species in the cells of a subject already afflicted with a disease resulting from oxidative stress, the progression of the disease may be inhibited. As described above, diseases which may result from oxidative stress include rheumatoid arthritis, lupus, and sickle cell anemia. The progression of the aforementioned diseases may therefore be inhibited by employing the subject method. Likewise, since oxidative stress results in damage to the DNA in cells, which consequently may result in the formation of tumors, the progression of diseases comprising the formation of tumors resulting from oxidative stress may also be inhibited by employing the subject method. Since the formation of tumors resulting from oxidative stress involves damage to DNA in cells, tumor formation resulting from oxidative stress includes tumors evolving from normal tissue as well as the enlargement of already developing tumors by damage to the DNA in cells surrounding the already developing tumor. As described above, diseases which comprise the formation of tumors include cancer.

In the above-described method, any suitable means known to those of ordinary skill in the art may be used to administer the pharmaceutical composition to the subject. In one embodiment, the pharmaceutical composition is topically applied to a part of the subject's body already manifesting the disease resulting from oxidative stress, e.g. to a tumor. However, topical application of the pharmaceutical composition to one part of the subject's body can be expected to have beneficial systemic effects on other parts, and thus the pharmaceutical composition need not be applied to the part of the subject's body manifesting the disease resulting from oxidative stress, should such a part exist. When the composition is topically applied, it may be in the form of a cream or a lotion.

In another embodiment, the pharmaceutical composition is orally administered to the subject. If oral administration is employed, the pharmaceutical composition may be in the form of a capsule, tablet, or solution.

In another embodiment, the pharmaceutical composition may be injected into the subject. Injection may be intramuscular, intraperitoneal, intravenous, or subcutaneous. The pharmaceutical composition may be injected into any part of the subject's body, including into a part manifesting the disease resulting from oxidative stress, e.g. a tumor.

As used herein, the term "pharmaceutically acceptable carrier" encompasses any of the standard pharmaceutically accepted carriers known to those of ordinary skill in the art. Examples of such standard carriers include, but are not limited to, phosphate buffered saline solution, water, emulsions such as oil/water emulsions or a triglyceride emulsion, various types of wetting agents, tablets, coated tablets and capsules. A suitable pharmaceutically accepted carrier may be selected taking into account the chosen mode of administration.

As used herein, the term "effective oxidative stress-inhibiting amount" is meant to indicate that amount which will inhibit the generation of reactive oxygen species in cells. The effective oxidative stress-inhibiting amount of the compound will depend on various factors known to those of ordinary skill in the art. Such factors include, but are not limited to, the size of the subject and the mode of administration. The effective oxidative stress-inhibiting amount of the compound will also depend on whether the pharmaceutical composition is to be administered a single time to the subject, or whether it is to be administered periodically over a stretch of time. A stretch of time may be any number of days, weeks, months, or years. In one embodiment, the oxidative stress-inhibiting amount of the compound may be between about 0.01 μg and about 20.0 μg per dose. Preferably the oxidative stress-inhibiting amount of the compound is between about 0.01 μg and about 10.0 μg per dose. Even more preferably, the oxidative stress-inhibiting amount of the compound is between about 0.02 μg and 2.0 μg per dose, this amount being especially preferred when the pharmaceutical composition is administered periodically, over a stretch of time.

In one embodiment of the above-described method of preventing in a subject a disease resulting from oxidative stress, the subject is a mammal. When the subject is a mammal, the subject may be a human being.

This invention further provides a method of treating a subject having an HIV infection which comprises administering to the subject a pharmaceutical composition comprising a pharmaceutically acceptable carrier, a substance which inhibits HIV replication, and an effective HIV integrase-inhibiting amount of a compound having the structure:

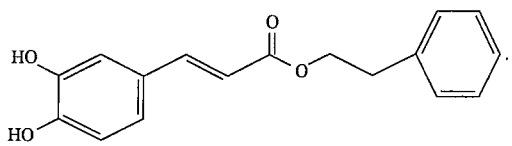

wherein

X and Y are independently carbonyl, C=S, S=O, or O=S=O; n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^8$ are independently $C_1$–$C_6$ linear or branched alkyl;

$R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, including, F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

In a preferred embodiment, n and p are 0, and $R_1$, $R_2$, $R_3$, $R_4$, and $R_5$ are hydrogen. In another preferred embodiment, n and p are 0; $R_1$, $R_2$, $R_3$, $R_4$, and $R_5$ are hydrogen; and $R_6$ is hexyl, butyl, ethyl, or phenylethyl.

In a further preferred embodiment, the compound has the structure:

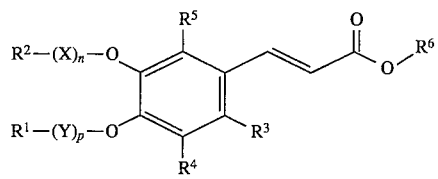

As the compound in the above-described method inhibits HIV integrase, the substance which inhibits HIV replication is preferably a substance which inhibits an enzyme in the HIV replication cycle other than HIV integrase. Preferably, the substance which inhibits HIV replication inhibits HIV reverse transcriptase. If the substance which inhibits HIV replication is a substance which inhibits HIV reverse transcriptase, it is preferably 3'-azido-3'-deoxythymidine.

In the above-described method, any suitable means known to those of ordinary skill in the art may be used to administer the pharmaceutical composition to the subject. In one embodiment, the pharmaceutical composition is topically applied to the subject. If the pharmaceutical composition is topically applied, the pharmaceutical composition may be in the form of a lotion or a cream. In another embodiment, the pharmaceutical composition is orally administered to the subject. If the pharmaceutical composition is orally administered, it may be in the form of a tablet, capsule, or solution. In another embodiment, the pharmaceutical composition is injected into the subject. The injection may be intravenous, intraperitoneal, intramuscular, or subcutaneous.

As used herein, the term "pharmaceutically acceptable carrier" encompasses any of the standard pharmaceutically accepted carriers known to those of ordinary skill in the art. Examples of such standard carriers include, but are not limited to, phosphate buffered saline solution, water, emulsions such as oil/water emulsions or a triglyceride emulsion, various types of wetting agents, tablets, coated tablets and capsules. A suitable pharmaceutically accepted carrier may be selected taking into account the chosen mode of administration.

As used herein, the term "effective HIV integrase-inhibiting amount" is intended to mean that amount which is effective to inhibit HIV integrase. The effective HIV integrase-inhibiting amount will depend on various factors known to those of ordinary skill in the art. Such factors include, but are not limited to, the size of the subject and the degree to which the HIV infection has already progressed in the subject. The effective HIV integrase-inhibiting amount of the compound will also depend on whether the pharmaceutical composition is to be administered to the subject a single time, or whether the pharmaceutical composition is to be administered periodically over a stretch of time.

In one embodiment of the above-described method of treating a subject having an HIV infection, the subject is a mammal. When the subject is a mammal, the subject may be a human being.

Finally, this invention provides a pharmaceutical composition for treating an HIV infection in a subject which comprises a pharmaceutically acceptable carrier, a substance which inhibits HIV replication, and an effective HIV integrase-inhibiting amount of a compound having the structure:

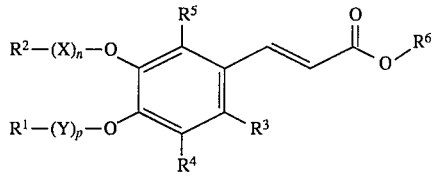

wherein

X and Y are independently carbonyl, C=S, S=O, or O=S=O; n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^8$ are independently $C_1$–$C_6$ linear or branched alkyl;

$R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_8$ linear or branched alkyl, alkenyl, or alkynyl; and $R_6$ is aryl or $C_1$–$C_{18}$ branched or linear alkyl, alkenyl, or alkynyl, either unsubstituted or substituted with halogen, including, F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

In a preferred embodiment, n and p are 0, and $R_1$, $R_2$, $R_3$, $R_4$, and $R_5$ are hydrogen. In another embodiment, n and p are 0; $R_1$, $R_2$, $R_3$, $R_4$, and $R_5$ are hydrogen; and $R_6$ is hexyl, butyl, ethyl, or phenylethyl.

In a further preferred embodiment, the compound has the structure:

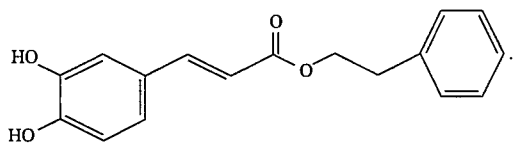

Preferably, the substance which inhibits HIV replication is a substance which inhibits HIV reverse transcriptase. If the substance which inhibits HIV replication inhibits HIV reverse transcriptase, it is preferably 3'-azido-3'-deoxythymidine.

As used herein, the term "pharmaceutically acceptable carrier" encompasses any of the standard pharmaceutically accepted carriers known to those of ordinary skill in the art. Examples of such standard carriers include, but are not limited to, phosphate buffered saline solution, water, emulsions such as oil/water emulsions or a triglyceride emulsion, various types of wetting agents, tablets, coated tablets and capsules. A suitable pharmaceutically accepted carrier may be selected taking into account the chosen mode of administration.

As used herein, the term "effective HIV integrase-inhibiting amount" is intended to mean that amount which is effective to inhibit HIV integrase. The effective HIV integrase-inhibiting amount will depend on various factors known to those of ordinary skill in the art. Such factors include, but are not limited to, the size of the subject, the degree to which the HIV infection has already progressed in the subject, and the pharmaceutically accepted carrier in the composition. The effective HIV integrase-inhibiting amount of the compound will also depend on whether the pharmaceutical composition is to be administered to the subject a single time, or whether the pharmaceutical composition is to be administered periodically over a stretch of time.

This invention will be better understood from the Examples in the "Experimental Details" Section which follows. However, one skilled in the art will readily appreciate that the specific methods and results discussed are merely illustrative of, and are not intended to, nor should they be intended to, limit the invention as described more fully in the claims which follow thereafter.

EXPERIMENTAL DETAILS

EXAMPLE 1

Chemicals and Reagents for In-Vivo Experiments on Mice and In Vitro Experiments. CAPE was obtained by esterification of caffeic acid with phenethyl alcohol in the presence of p-toluenesulfonic acid as the catalyst (1). A.S.A.P. DNA purification columns and the enzymes used for purification and enzymatic hydrolysis of DNA (proteinase K, RNase, DNase I, nuclease $P_1$, and alkaline phosphatase) were purchased from Boehringer-Mannheim Biochemicals (Indianapolis, Ind.). Other reagents and enzymes (such as glucose, glucose oxidase, horseradish peroxidase (HRPO), and 2',7'-dichlorofluorescin diacetate) were purchased from Sigma Chemical Co. (St. Louis, Mo.), and HPLC-grade acetonitrile and acetone were from Fisher Scientific (Springfield, N.J.).

EXAMPLE 2

Radioactive Materials for In Vivo Experiments on Mice and In Vitro Experiments. [³H]acetic anhydride (specific activity, 50 mCi/mmol) was obtained from Du Pont New England Nuclear (Wilmington, Del.). Nonradioactive caffeic acid, HMdUrd, and TPA were purchased from Sigma. TPA was also purchased from CRC, Inc. (Chanhassen, Minn.). 8-OHdGua was synthesized according to published procedures (49, 50), while the marker acetates were prepared by acetylation of HMdUrd and 8-OHdGua with acetic anhydride in the presence of a catalyst in dry acetonitrile (49, 51). The products were purified by high performance liquid chromatography (HPLC) and their identity confirmed by mass spectroscopy (50).

EXAMPLE 3

In Vivo Experiments on Mice:

A) Treatment of Animals and Assays. Female SENCAR (6–8 weeks old) and CD-1 mice (about 7 weeks old) were purchased from Biological Testing, National Cancer Institute (Frederick, Md.) and from Charles River Laboratory (Stone Ridge, N.Y.), respectively. The mice were acclimated for at least 1 week before use. They were subjected to a 12-h light/12-h dark cycle, housed at 20°±2° C. in a room with 10 cycles of air exchanges/h, given food and water ad libitum, and observed for any indication of ill health. Before topical application of any test agents, their backs were shaved and only those without hair growth after 48 h were used.

B) Edema Determination. Both ears of SENCAR mice (7–9 mice/group) were treated with 0.4 nmol TPA in 20 μl acetone alone or together with added 0.1 nmol, 0.3 nmol, or 1 μmol CAPE. Control mice were treated with acetone. The mice were sacrificed by cervical dislocation 5 h after treatment, and edema was measured on one mouse ear, while the second ear was immediately frozen and later analyzed for PMN infiltration by quantifying myeloperoxidase (MPO) (see below). Ear edema (increased weight of ear punches) was determined as previously described (24). Edema was expressed as mg/6 mm (diameter) ear punch±SE.

C) MPO, $H_2O_2$, and Oxidized DNA Bases. SENCAR mice were pretreated with CAPE for 30 min; then 6.5 nmol (4 μg) TPA/mouse topically applied to the dorsal skin. After 20 h, the CAPE and TPA treatment (1x) was repeated (2x treatment). One h after the second treatment, the mice were sacrificed by cervical dislocation, and 12.5-mm punches were obtained to be used separately for MPO and $H_2O_2$ determinations. The remainder of the treated mouse skin or the combined skins from two mice were used for separation of epidermal cells. This was done by heating the skin at 55° C. for 30 s followed by rapid immersion into an ice-cold water bath (45). After the epidermis was scraped off, the presence of oxidized DNA base derivatives was measured in the epidermal DNA. All of these end points were analyzed by published procedures and are briefly described below.

The assay for MPO was carried out according to the procedure of Metcalf et al. (53) with some modifications (20), and the results are expressed as units/cm$^2$, where a unit is defined as that degrading 1 μmol $H_2O_2$/min at 25° C. The presence of MPO in the mouse ears was measured in the homogenates. They were prepared by mincing the ears and homogenizing them in an ice-cold water bath with a polytron homogenizer, either twice for 20 s each or three times for 10 s each. Each homogenate was analyzed in duplicate and the results are expressed as mean MPO (units/mg protein) ±SE for each of the homogenates. In this case, SE shows reproducibility of each MPO analysis.

Punches used for $H_2O_2$ determination were immediately minced with scissors in cold 50 mM phosphate buffer, pH 7.0, containing 10 mM azide that is needed for inhibition of catalase. They were then homogenized, and centrifuged at 4° C. and the supernatants were stored at −80° C. for up to 1 week. $H_2O_2$ was measured in freshly thawed supernatants using horseradish peroxidase-mediated oxidation of phenol red (21), and the results are expressed as nmol $H_2O_2$/cm$^2$/ 10-min incubation. Although organic hydroperoxides also can be generated under these conditions (45), we find that $H_2O_2$ constitutes a great majority of the oxidants generated because 60–85% of the oxidants produced are catalase inhibitable (21).

The epidermis was homogenized and lysed, and the proteins and RNA were removed by proteinase K and RNase digestions, respectively (20). The DNA was separated and purified on A.S.A.P. columns (Boehringer-Mannheim Biochemicals) and precipitated with isopropyl alcohol.

The pellet was then washed with 70% ethyl alcohol, dried, and dissolved in 10 mM Tris•HCl-100 mM NaCl buffer, pH 7.0, according to the manufacturer's procedure. The DNA was sheared and enzymatically digested to nucleosides, and the hydrolysates were separated by HPLC (Beckman, Model 344) on an ODS column (Altex, 1×25 cm; 5 μm particle size) (50). The fractions that eluted after 30 ml were combined (excluding those containing normal nucleosides) and dried. The oxidized nucleosides were detected by $^3$H-postlabeling with [$^3$H]acetic anhydride, followed by HPLC analysis of $^3$H-containing acetates in the presence of marker acetates (50). The results are presented as the number of oxidized nucleosides/10$^4$ normal bases, unless otherwise stated.

EXAMPLE 4

In Vitro Experiments:

A) Human PMNS Blood was obtained from healthy volunteers and collected into EDTA-containing tubes. Red cells were removed by dextran sedimentation and lysis with hypotonic ammonium chloride, as described previously (5). Cells were washed in glucose-containing basic salt solution (137 mM NaCl, 5 mM KCl, 8.5 mM $Na_2HPO_4$-$NaH_2PO_4$, 0.8 mM $MgSO_4$, 5 mM glucose, pH 7.4) and suspended at a ratio of 10 ml of the initial blood volume/ml basic salt solution. Whole WBC population was used as a source of PMNs, with PMN numbers used per assay being adjusted according to the results of Wright's staining of the peripheral blood.

PMNs ($2.5 \times 10^5$/ml) were incubated with CAPE (0.05–5.0 nmol/ml) and/or TPA (25 pmol/ml) at 37° C. for 30 min in the presence of phenol red (100 μg) and HRPO (50 μg) (54). After the reaction was stopped with catalase (50 μg/ml), the pH was adjusted to 12.5 with NaOH, the mixture was centrifuged, and the absorbance of the supernatant was determined at 598 nm. The concentration of $H_2O_2$ produced was established from the standard curve.

B) Bovine Lens Bovine lenses were obtained from a New Jersey slaughterhouse 3 h after the animals were sacrificed. Lenses were immediately immersed in artificial aqueous humor (AAH; 130 mMNaCl, 5 mMKCl, 1 mM $CaCl_2$, 0.5 mM $MgCl_2$, 10 mM $NaHCO_3$, 10 mM 4-(2-hydroxyethyl)-1-piperazineethanesulfonic acid (pH 7.3), and 2.5 mM D-glucose). Each of the bovine lenses in AAH (about 15 ml/lens) supplemented with 10 mM azide (a catalase inhibitor) was incubated with various amounts (0–1 μM) TPA at 37° C. for 24 h in the presence or absence of CAPE (1 μM), as described for use of other chemopreventive agents (31). For comparison, the lenses were also incubated with glucose (2.5 mM)/glucose oxidase (25 μM), a $H_2O_2$-generating system.

After incubation, lenses were homogenized in 15 ml of azide-supplemented AAH in a Waring Blender, and $H_2O_2$ content was determined spectrofluorometrically, as described previously (55). Briefly, the homogenates were incubated with 2',7'-dichlorofluorescin diacetate, which is deacetylated by the esterase present in the homogenate. In the presence of HRPO, the nonfluorescent substrate was oxidized by $H_2O_2$ generated in the lens to a highly fluorescent product, which was measured at excitation 475 nm and emission 525 nm (30, 31, 55). The amount of $H_2O_2$ generated was determined from a standard curve, which was constructed by addition of increasing concentrations of $H_2O_2$ to a homogenate derived from a control lens incubated only in AAH.

In some experiments, at the end of incubation [lenses in (a) AAH only (controls), (b) AAH+0.1 μM TPA, and (c) AAH+1 μM CAPE (30 min)+0.1 μM TPA] at 37° C. for 24 h, the lenses were photographed against a 3-mm grid.

EXAMPLE 5

In Vivo Experiments on Rabbits

A) chemicals and reagents. 12-O tetradecanoylphorbol-13 acetate (TPA) was purchased from LC Services Corp. (Woburn, Mass.). CAPE was synthesized as described, basically by acid-catalyzed esterification of caffeic acid with phenethyl alcohol (1).

B) Test animals. Six healthy young (6–8 weeks old) white New Zealand rabbits of both sexes were used for the experiments. Each animal had normal eyes as confirmed by ocular examination by slit lamp.

C) Treatment of animals and monitoring the eye alterations. Cataracts were induced by the direct application of both TPA and CAPE into the eye chamber. On every third day, 0.05 ml of the TPA solution (200 µg/ml PBS) was injected into the anterior chamber of both eyes via a puncture at the corneo-scleral limbus with a fine 0.3×42 mm needle joined to a tuberculin syringe. The animals were all given local anesthesia with HUMACAIN eye drops (human, Gödöllö, Hungary) under sterile conditions for each application. One hour after TPA was injected, 0.05 ml of the CAPE solution (50 µg/ml) was administered into the anterior chamber of only the left eye, as above. The right eye of each animal received no further treatment. This procedure was repeated a total of 16 times. Periodic ocular examinations by slit lamp were performed after the 6th, 12th, and final drug applications. Subsequently, examinations were made on the 10th and 23rd days after the last drug treatment. After each ocular examination, the physical findings were recorded and photodocumentation of the eye changes were performed. The photographic documentary was executed in the following manner. Firstly, lenses were illuminated by a fiber optic light source from behind and photographs were taken from a distance of 5–6 cm. The diapositive black and white images on paper were transferred into an IBM personal computer (system 2, model 30) using a Sony-2-Cue CCD video camera that was equipped with Fujinon TV zoom objective (1:1.8) via a 17.5-105 signal-transfer system. Finally, with these computer image reconstructions, the areas of the lens opacifications were delineated and quantified using the Olympus image analyzer C-2 morphometry version 2.2 program.

RESULTS

Figure 2A:
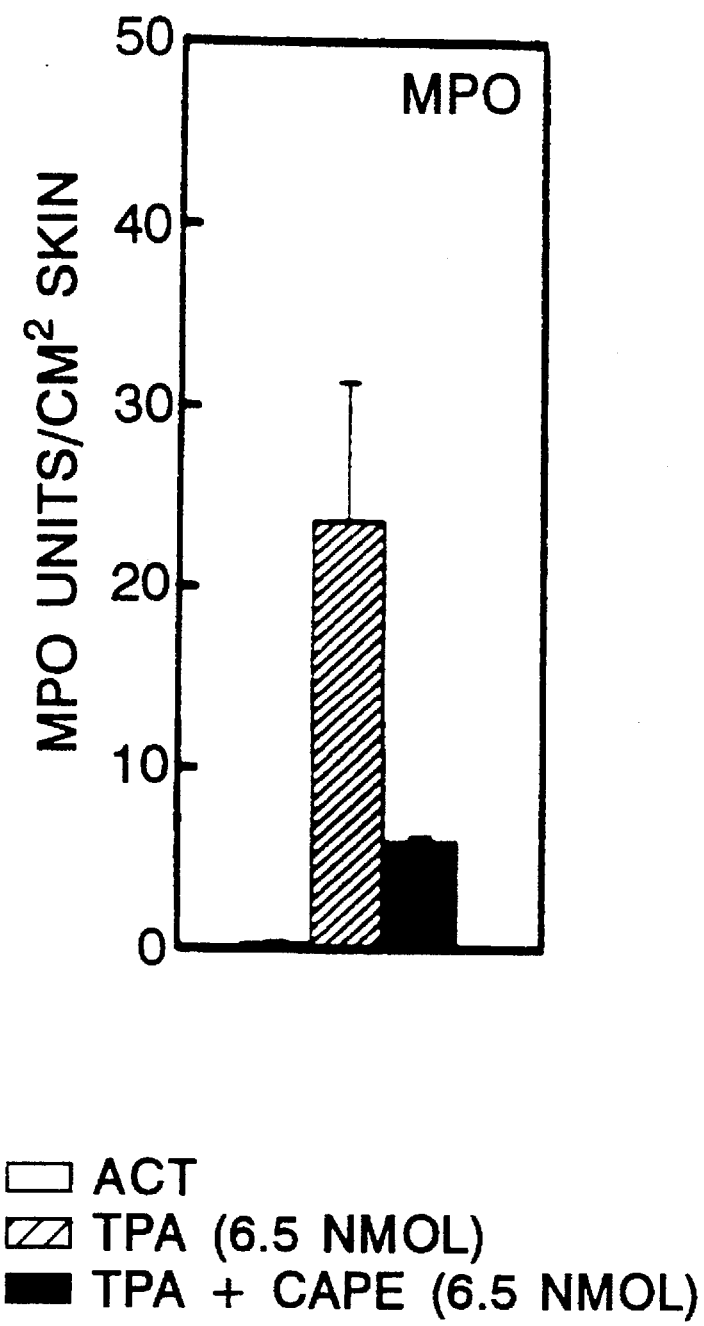
Figure 2B:
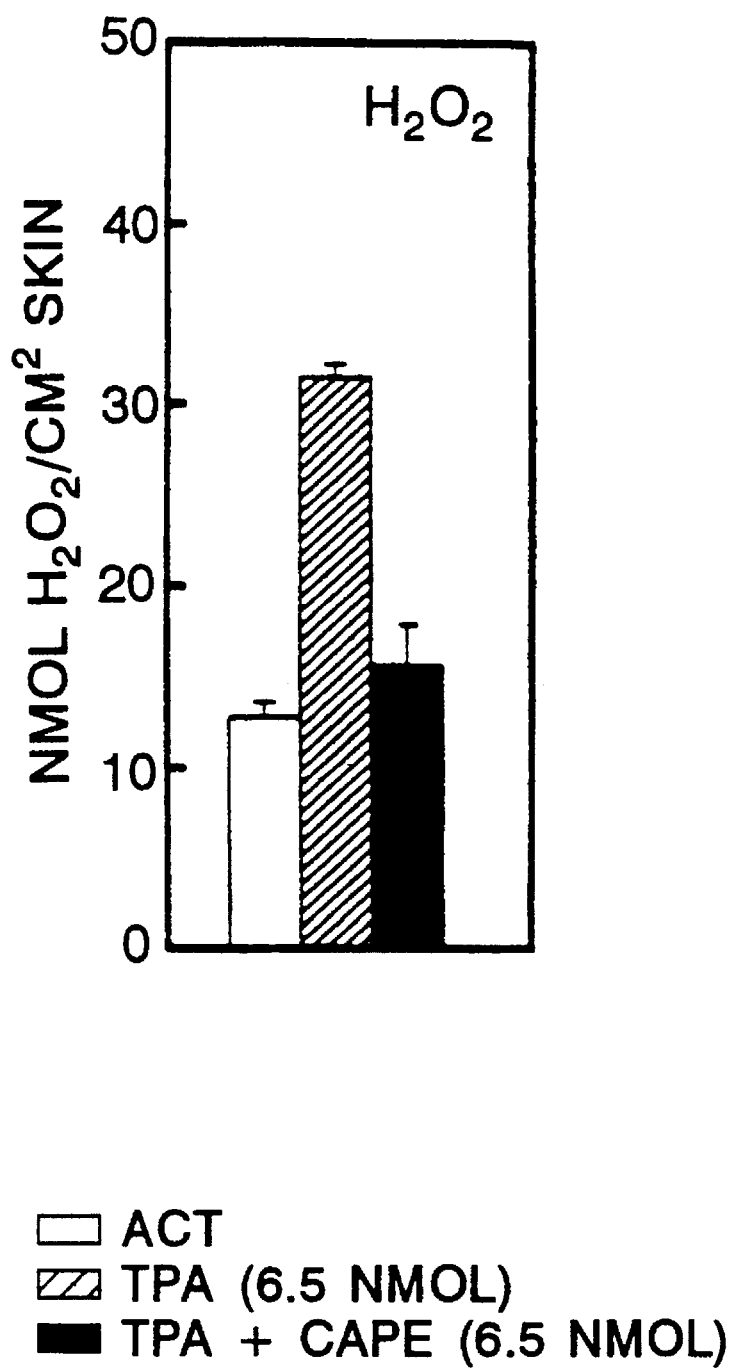
Figure 2C:
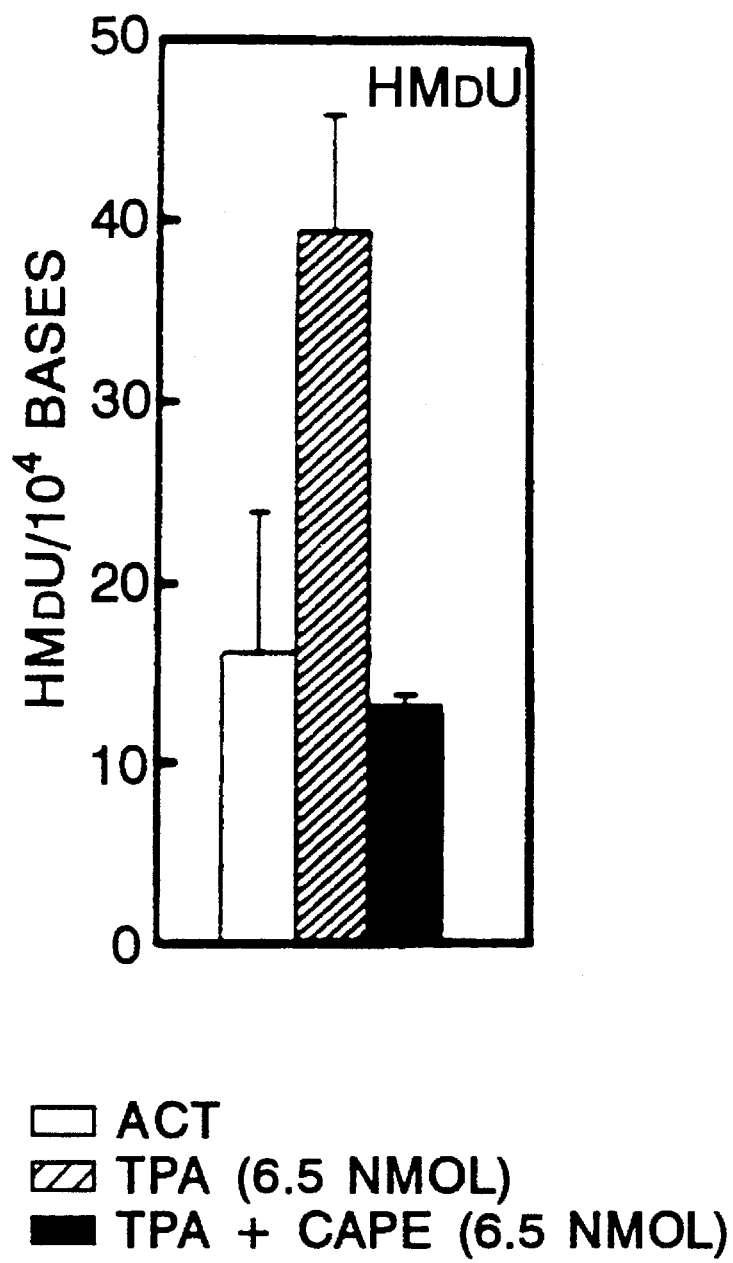
Figure 2D:
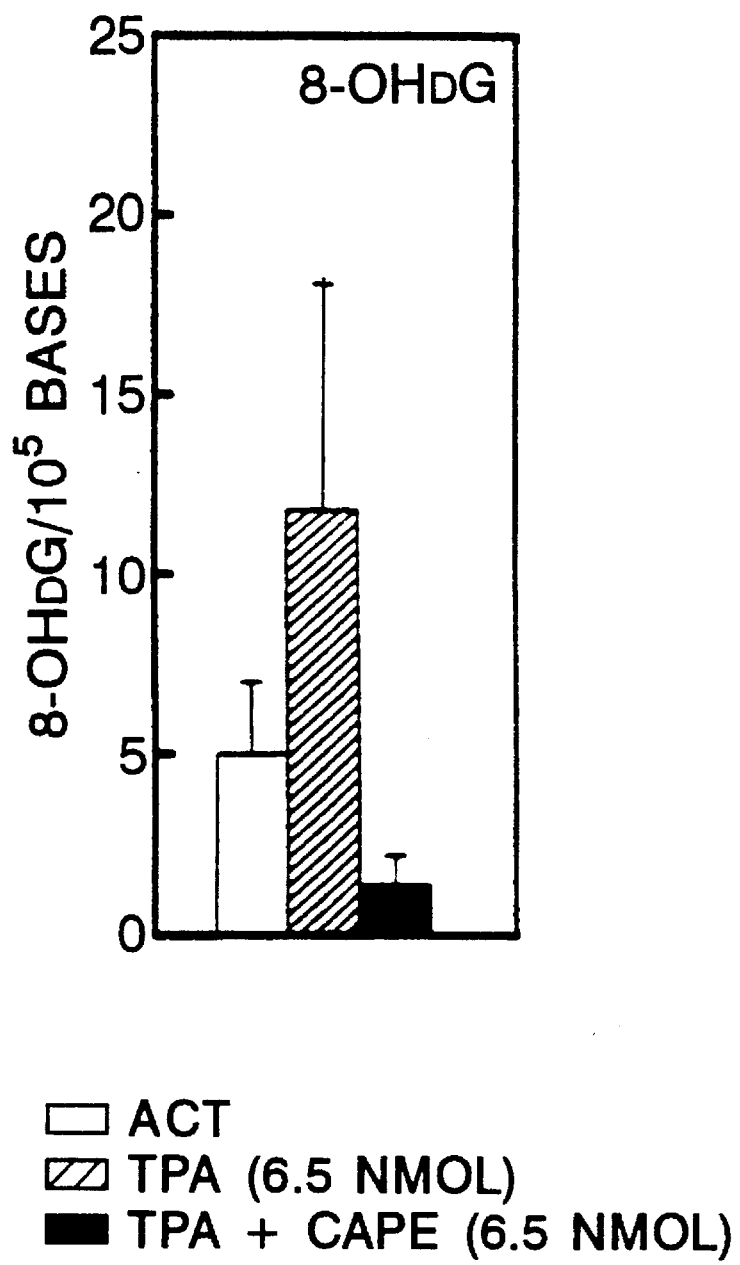

CAPE-mediated. Inhibition of TPA-induced PMN Infiltration, $H_2O_2$ Production, and Formation of HMdUrd and 8-OHdGua in Mouse Skin. When SENCAR mice were treated with CAPE (6.5 nmol) 30 min prior to each of two TPA (6.5 nmol) applications, a number of inhibitory processes occurred and are shown in FIGS. 2A–2B. Treatment of mice with CAPE decreased TPA-induced PMN infiltration by ≈85%, as quantified by the presence of MPO (FIG. 2A), an enzyme characteristic of PMNs (59). Although other cell types (i.e. monocytes) also contain MPO (59), treatment of mice was so short (21 h total), that it is unlikely that cells other than PMNs would infiltrate the mouse skin in significant amounts during that time. Concurrently, topical application of CAPE also almost completely (86%) inhibited TPA-induced $H_2O_2$ formation (FIG. 2B). HMdUrd levels were decreased by CAPE (FIG. 2C) below the acetone/acetone controls, while 8-OHdGua levels were suppressed significantly (70%) below controls (FIG. 2D).

The CAPE-mediated decrease of the levels of oxidized bases below the acetone/acetone controls indicated that the following have occurred: (a) acetone treatment evoked a weak inflammatory response; and/or (b) CAPE inhibited some normal oxidative processes in mouse skin as well. To resolve this, additional controls were carried out. SENCAR mice, which were shaved 48 h before the experiment, were not treated with anything (blanks), and the MPO and 8-OHdGua levels were compared to mice treated with acetone. The 8-OHdGua level present in the epidermal DNA of the blanks was 65–70% lower than in the DNA of control acetone-treated mice. These results show that acetone treatment of control mice is already somewhat inflammatory. Secondly, CAPE inhibits the inflammatory processes down to the background levels represented by untreated blanks, particularly the oxidation of bases in DNA.

Figure 3:
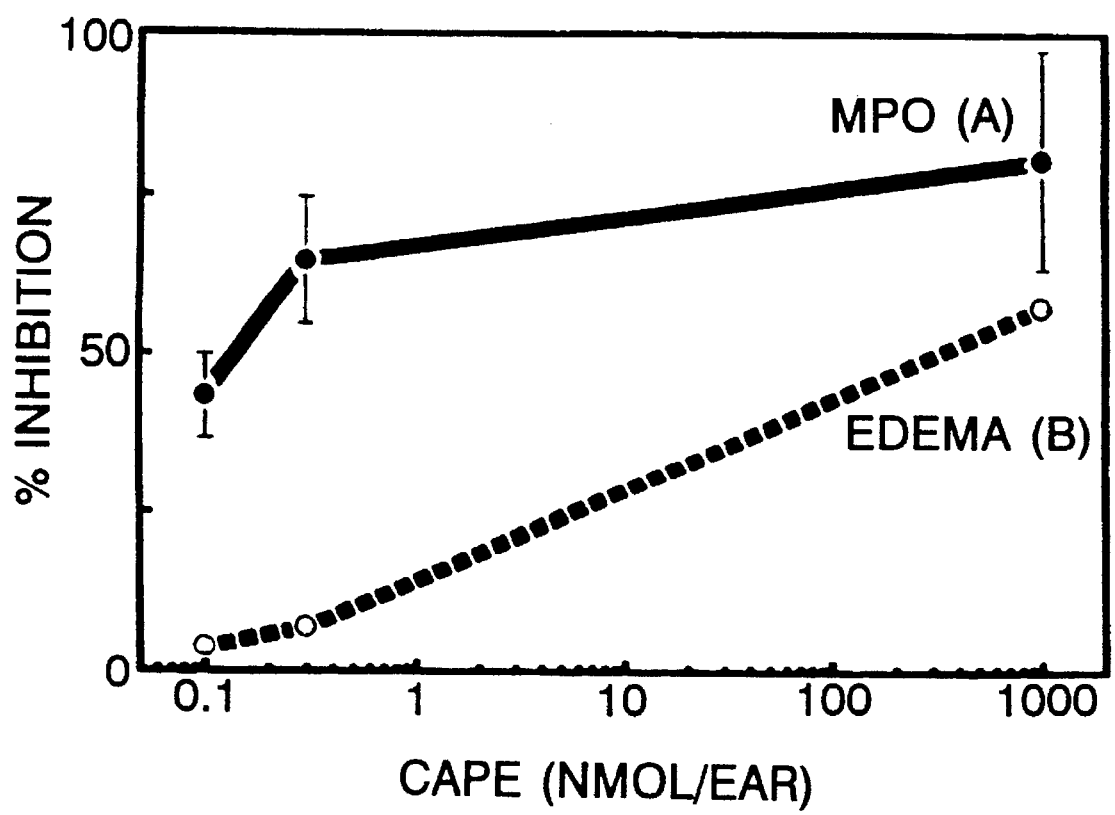
FIG. 3. Effect of CAPE on TPA-induced PMN infiltration and edema in SENCAR mouse ears. These were paired experiments, in which both ears of each mouse (8–9/group) were treated with 0.4 nmol TPA±CAPE in 20 µl acetone, and the mice were sacrificed 5 h later. (A) One ear was frozen for subsequent determination of MPO (a measure of PMN infiltration). (B) A punch (6 mm diameter) was taken from the second ear and weighed to measure edematous response (weight of sample minus weight of control). (A) Ears of each group (7–9/group) were separately minced and homogenized under different conditions as described in the "Experimental Details" Section, infra. MPO was determined in duplicate. MPO was undetectable in acetone controls and was 4.13±0.0 units/mg protein and 1.18±0.1 units/mg protein in the 2 homogenates of TPA-only-treated mice. CAPE-mediated inhibition was calculated versus the appropriate TPA-only sample, which was homogenized the same way. (B) Weights of ear punches (8–9/group, each determined separately). Acetone controls, 7.2±0.1 mg; TPA in acetone, 16.7±0.7 mg.

Infiltration of phagocytic cells and induction of edema have been used as measures of tumor promoter-mediated inflammatory responses (3, 25, 45, 46, 60). Therefore, it was puzzling why a low dose of 6.5 nmol CAPE suppressed TPA-mediated PMN infiltration into mouse skin by 85% (FIG. 2A), whereas over a 100-fold higher dose has been demonstrated as required to comparably inhibit ear edema in the same mouse strain (76). This could be because different sites were being analyzed, i.e. skin on the back of the mouse versus ears. Another possible explanation would be if PMN infiltration was much more sensitive to the action of chemopreventive agents than edema in general. To determine which of the two possibilities is more likely to be the contributing factor, both ears of SENCAR mice were simultaneously treated with CAPE/TPA. Ear punches from one ear were weighed to measure edema, and the other ear was used to determine MPO levels, a measure of PMN infiltration. FIG. 3 shows the results of those paired experiments. It is apparent that under the same treatment conditions, CAPE suppressed TPA-induced PMN infiltration nearly 50% at 0.1 nmol of CAPE/ear, while a dose 4 orders of magnitude higher (1 µmol) was needed for similar inhibition of edema.

Figure 4:
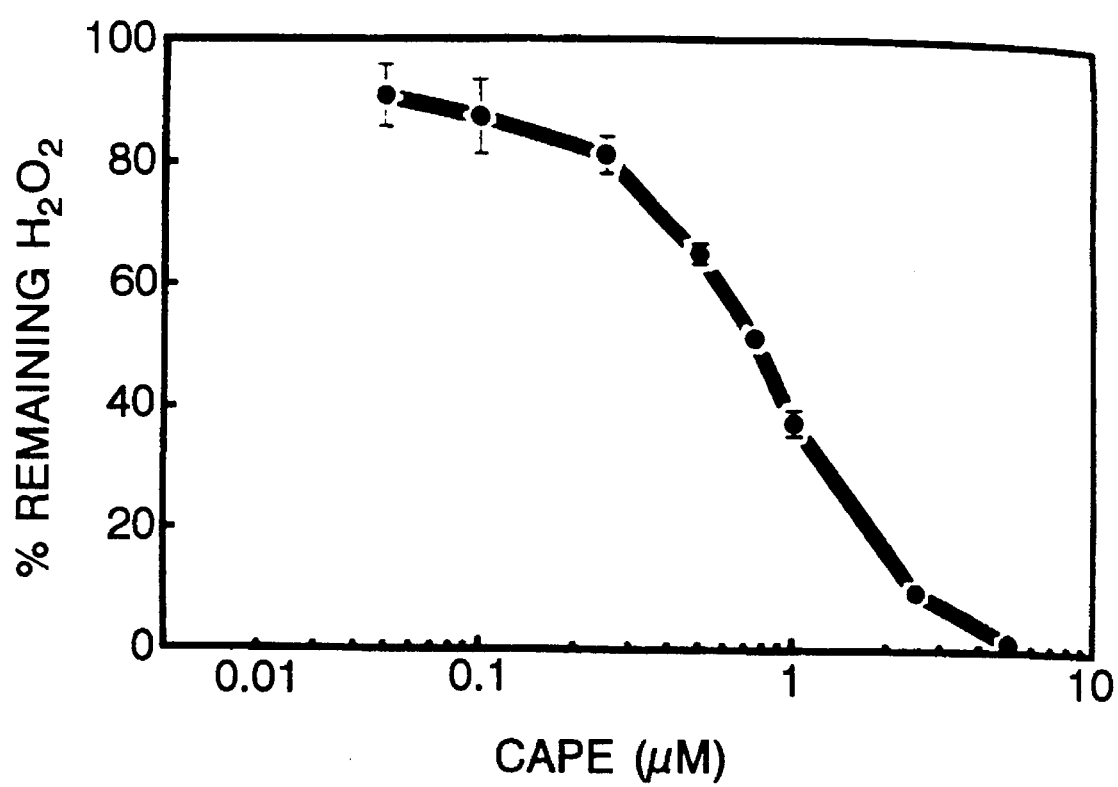
FIG. 4. CAPE-mediated inhibition of $H_2O_2$ formation by TPA-stimulated human PMNs. Cells were incubated with CAPE (0.05–5 nmol/ml) and TPA (25 pmol/2.5×10$^5$ PMNs/ml) at 37° C. for 30 min, and $H_2O_2$ was determined by the phenol red/HRPO assay, as described in the "Experimental Details" Section, infra. Note the semilog scale. The results are presented as mean values ±SE.

Inhibitory Effect Of CAPE On TPA-mediated $H_2O_2$ Production by Human PMNs in Vitro. It was shown previously that the levels of oxidized bases in DNA depend on the amounts of $H_2O_2$ generated (21, 22, 54). A decrease in the $H_2O_2$ produced could be due to the decreased infiltration of PMNs. However, it also could be due to the CAPE-mediated inhibition of TPA-induced oxidative burst of PMNs. To determine the latter, human PMNs were pretreated with various doses of CAPE (0.05–5.0 nmol CAPE/$2.5\times10^5$ PMNs/ml) prior to TPA application (25 pmol TPA/$2.5\times10^5$ PMNs/ml). FIG. 4 shows that similar to other chemopreventive agents, CAPE inhibited the oxidative burst of PMNs (as measured by $H_2O_2$ production) in a dose-dependent manner, with 50% inhibition at 0.5 nmol CAPE/ml. This makes CAPE one of the most potent inhibitors of the oxidative burst that we have analyzed (28, 60–63). Since CAPE does not degrade $H_2O_2$ or inhibit HRPO (R. Bhimani and K. Frenkel, unpublished results), it is probable that CAPE acts by inhibiting reactive oxygen species production by TPA-activated PMNs.

Inhibitory Effect of CAPE on TPA-mediated Induction of $H_2O_2$ in Bovine Eye Lens. We decided to find out whether CAPE could also inhibit oxidative stress [known to contribute to cataract formation (39)] in the eye lens. First, we had to establish whether TPA can induce oxidant production in the lens. TPA is known to cause $Ca^{2+}$ mobilization in a variety of cells (37–40), and $Ca^{2+}$ was shown to play a role in the development of cataracts (39, 68, 69).

The concentration of $H_2O_2$ was measured in lens homogenates after treatment of the whole lens with TPA or glucose/glucose oxidase, a $H_2O_2$-producing enzymatic system. As Table 1 shows, the 24-h incubation with TPA resulted in increased formation of $H_2O_2$ in the bovine lens in a dose-dependent manner, with 0.05, 0.1 and 1.0 µM TPA causing about 2-, 3.5- and 7-fold increases in the concentration of $H_2O_2$ over that present in control lenses in the absence of TPA. Table 1 also shows that 0.1 µM TPA-induced $H_2O_2$ was generated at comparable levels to those produced by glucose/glucose oxidase. Pretreatment of lenses with 1 µM CAPE for 30 min followed by co-incubation with 0.1 µM TPA for 24 h caused a decline in TPA (0.1 µM)-induced $H_2O_2$ production by about 95% (Table 1).

TABLE 1

$H_2O_2$ formation in bovine lens incubated with either TPA, glucose/glucose oxidase and inhibitory effect of CAPE[a]

| Treatment | $H_2O_2$ (µM) | % of change from control |
|---|---|---|
| Control[b] | 11.9 ± 1.2 | |
| Glucose/glucose oxidase | 43.2 ± 1.3 | 365 |
| 0.01 µM TPA | 11.3 ± 0.2 | 95 |
| 0.05 µM TPA | 23.3 ± 1.3 | 200 |
| 0.10 µM TPA | 42.7 ± 1.6 | 360 |
| 1.0 µM TPA | 83.8 ± 5.6 | 705 |
| 1 µM CAPE/0.1 µM TPA | 13.1 ± 1.3 | 110 |

[a]After treatment, lenses were homogenized as described in "Materials and Methods," and $H_2O_2$ concentration was determined by formation of fluorescent 2',7'-dichlorofluorescein. The fluorescent intensity of whole lens homogenate is proportional to $H_2O_2$ concentration, which was obtained from a calibration curve. The results are expressed as mean of 3 experiments ± SE.
[b]Lenses were incubated in artificial aqueous humor only.

Figure 5A:
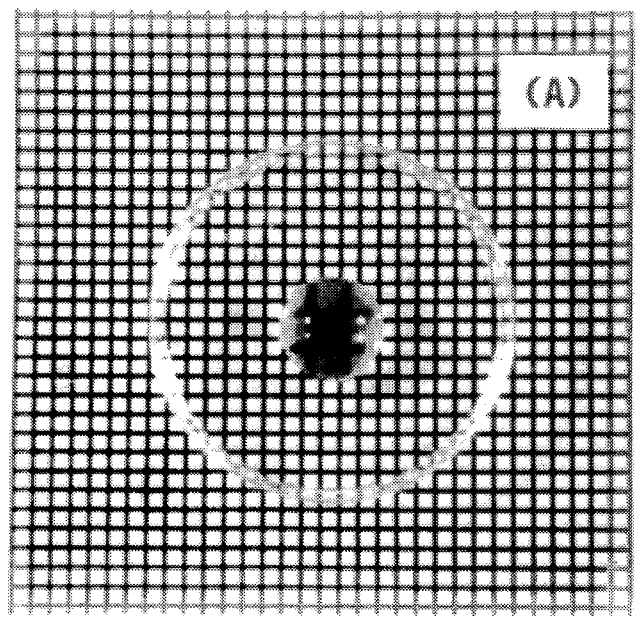
FIGS. 5A–5C. CAPE-mediated protection of bovine lens from TPA-induced opacity. Lenses were incubated with artificial aqueous humor only (FIG. 5A); incubated with 0.1 µM TPA (FIG. 5B); and pretreated with 1 µM CAPE for 30 min followed by 0.1 µM TPA (FIG. 5C) for 24 h. After incubation, the lenses were photographed against 3-mm grids.
Figure 5B:
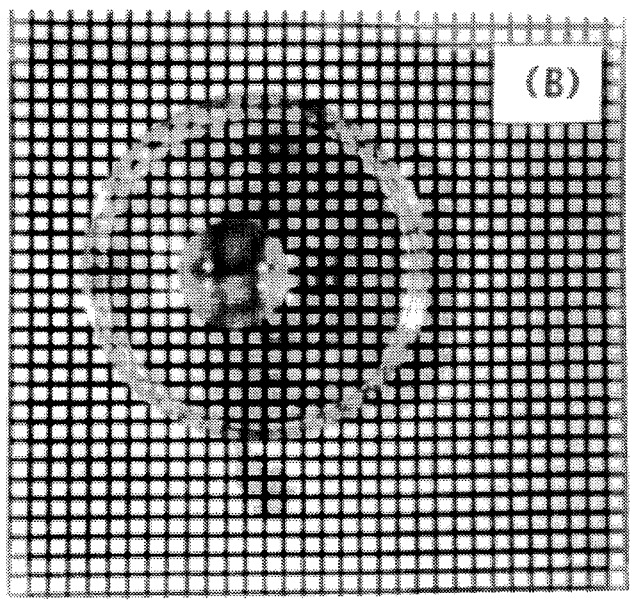
Figure 5C:
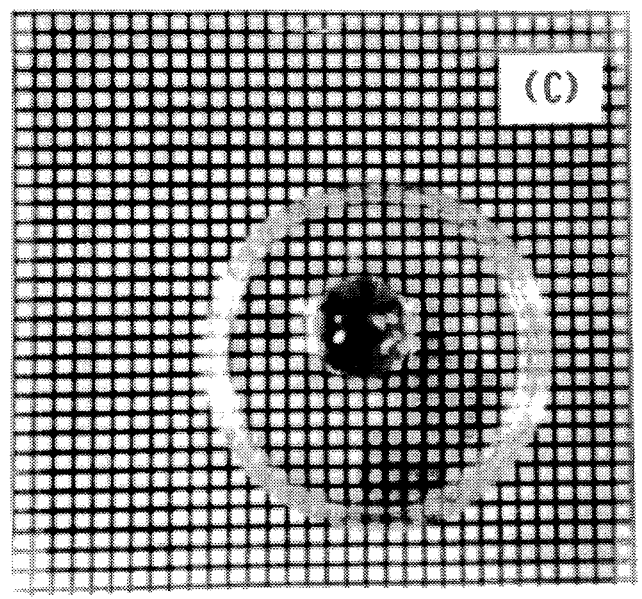

FIGS. 5A–5C show the results of experiments in which the whole lens was incubated with AAH only (control, FIG. 5A), or with 0.1 µM TPA in the absence (FIG. 5B) or presence of 1 µM CAPE (FIG. 5C) for 24 h. Already at 0.1 µM, TPA caused opacity of the lens (FIG. 5B), which was even more pronounced when the lens was incubated with 1 µM TPA (31). At the concentration used, CAPE almost completely prevented opacification of the lens.

Inhibitor Effect of CAPE on TPA-induced Cataracts In vivo, Since the daily application of a TPA-containing drops into the eyes of rabbits during a 6 week period failed to induce any visible alteration in the transparency of the lenses in any of the treated animals, TPA was injected directly into the anterior eye chambers. The pathological effects of this approach were clearly manifested. Cataracts of various sizes and types were evident by ocular examination in both eyes starting after the 12th TPA injection. Progression of the cataract development occurred during the phases of subsequent drug treatments and during the 33 days after these treatments. Physical changes included an increasing size of the cataracts, the deeper extension of the cataracts into nuclear portions of the lenses, and the maturation of some of the cataracts. Comparing the lens appearance of both eyes of each animal, the left eye that received CAPE was significantly clearer, having been spared the extensive opacification induced by TPA exposure. In fact, it was apparent by the 12th treatment period that CAPE injections to the left eyes of animals produced a prophylactic effect on incipient cataracts.

Figure 6:
FIG. 6. The TPA-treated right eye of rabbit No. 5 at the termination of the experiment. Specifics relating to the photography are defined in the "Experimental Details" Section, infra.
Figure 7:
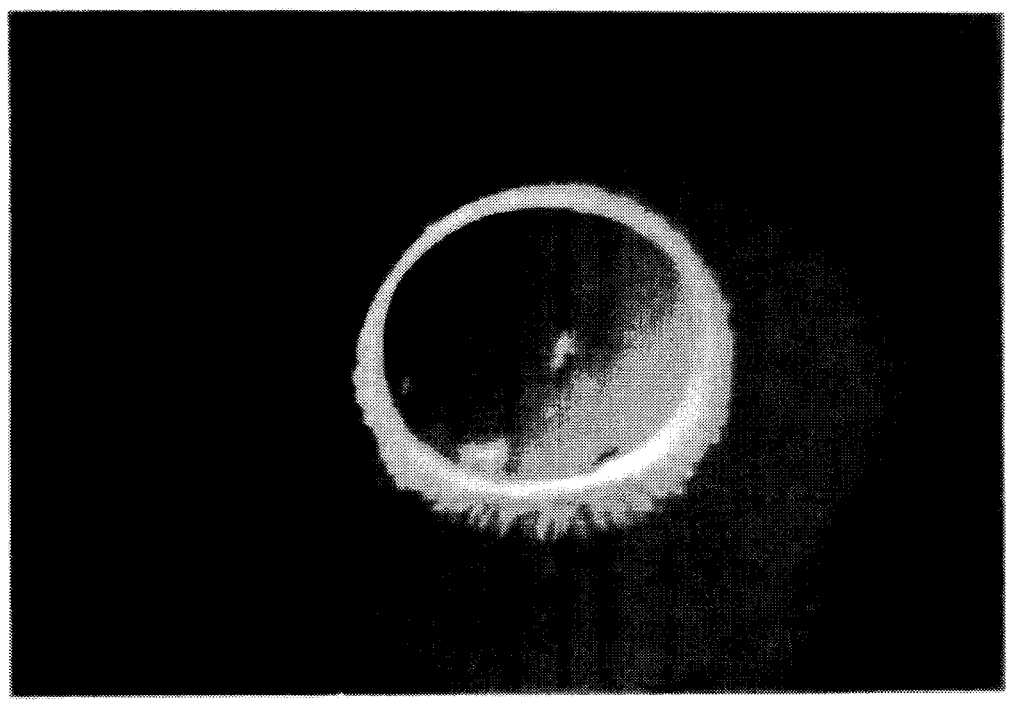
FIG. 7. The TPA plus CAPE-treated left eye of the same test rabbit (shown in FIG. 6) at the conclusion of the experiment.

The effects of the TPA and TPA plus CAPE injections appear in FIGS. 6 and 7. FIG. 6 shows the TPA-treated right eye of rabbit No. 5 at the conclusion of the experiment. In the center of the lens, a rather large arched subcortical condensed immature but developing cataract is evident. It appears to be spreading toward the nuclear region. At the 8 o'clock position, 3 small cortical punctiform opacities are present, and at the 11 o'clock position 2 subcortical condensed immature dot-like cataracts are visible. In contrast, FIG. 7 shows the CAPE-treated left eye of the same animal. In the center of this eye, a small capsular-subcapsular immature cataract is evident. Additionally, at the 7 o'clock position of the lens rim another subcapsular immature linear cataract is present as well as another very small circumscribed subcapsular immature cataract situated nearby and above it.

Similar results were obtained in the other test animals. In the CAPE-treated eyes cataracts were visible, but they were generally smaller and more immature. Specifically, the cataracts in the CAPE-treated eyes were all sharply delineated and mostly superficial cortical and subcapsular in nature. Conversely, the eyes that receive TPA alone showed larger, more mature cataracts that had spread deeply into the nuclear region.

Figure 8:
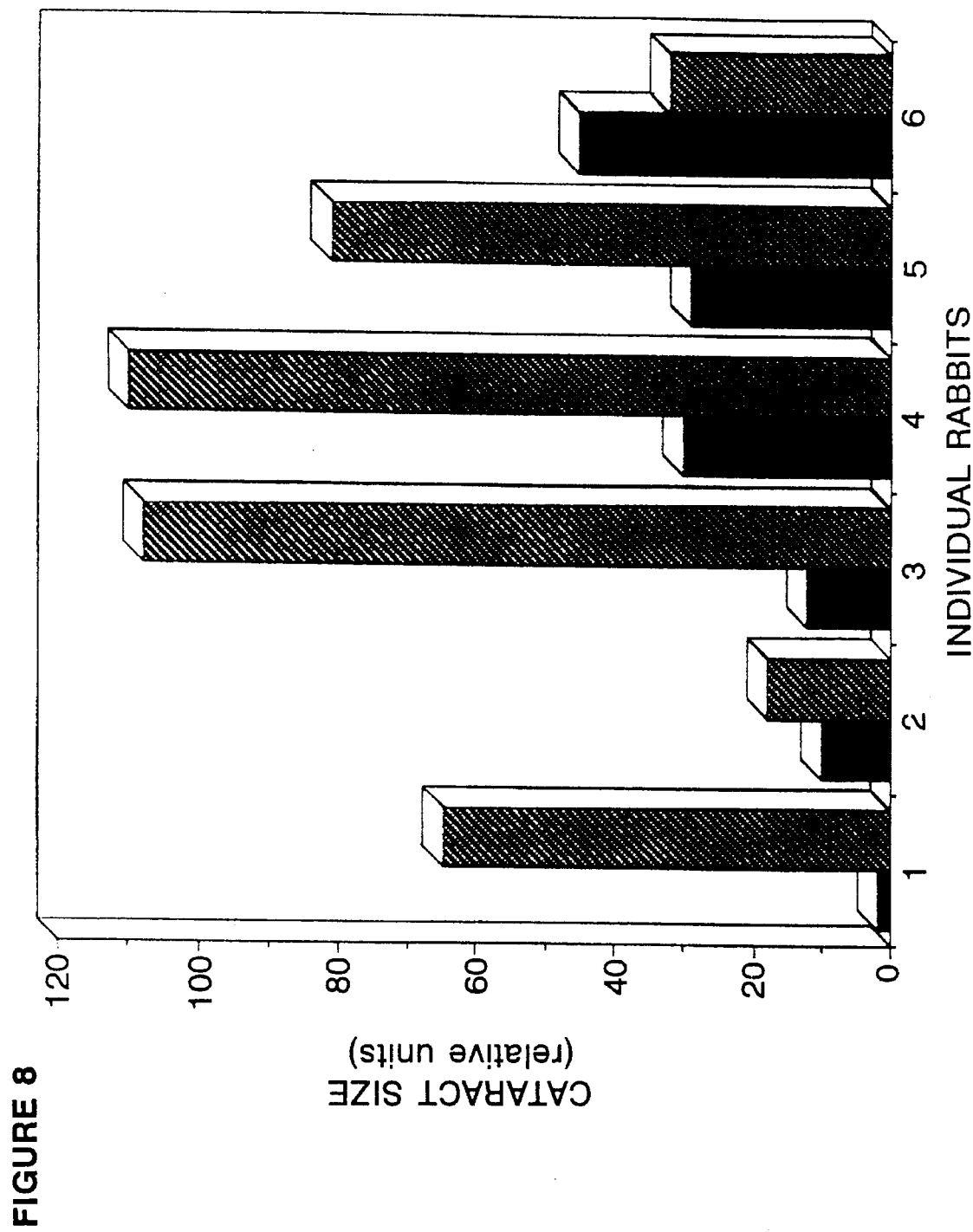
FIG. 8. Histogram showing cataract sizes in relative units for all of the test rabbits at the termination of the experiment. The solid bars (■) indicate the left eye treated with TPA and CAPE. ■ indicates the right eye, treated with TPA only.

The differences in the cataract appearances for the two treatments was quantitated by morphometrical computer analysis at the termination of the experiment. The area of the TPA-induced cataracts proved to be much larger (2.2–44.2 times) in the eye that did not receive CAPE than in the one injected with this compound. This result was obtained in 5 out of the 6 test animals and is shown in FIG. 8. In only a single rabbit was the cataract size in the CAPE-treated contralateral eye larger than that noted in the right one. By the Student's t-test, these differences quantitated by morphometry were highly significant ($p<0.001$). The quantitative basis for FIG. 8 is presented in Table 2. The cataract sizes are represented in relative units and the percent of CAPE-treated cataracts are compared with the control right eye of each animal.

TABLE 2

| | Size of cataract in relative units. | | |
|---|---|---|---|
| Animal | Control[1] | CAPE[2] | % of Control |
| 1 | 63.139 | 1.428 | 2.25 |
| 2 | 14.704 | 6.739 | 45.83 |
| 3 | 104.97 | 10.77 | 10.26 |
| 4 | 111.62 | 28.722 | 25.73 |
| 5 | 99.923 | 30.199 | 30.22 |
| 6 | 28.578 | 43.184 | 151.11 |

[1]TPA-treated right eye.
[2]TPA + CAPE treated left eye of the same animal.

DISCUSSION

Propolis, which is a product of honeybee hives, has been used for centuries in folk medicine as an anti-inflammatory agent (1). CAPE, which is an active ingredient present in propolis, is not toxic to normal tissue. We have shown that CAPE is a potent inhibitor of a number of oxidative processes both in vitro and in vivo even at very low doses (0.1–6.5 nmol/treatment). These processes include: (a) tumor promoter-mediated PMN infiltration into mouse skin and mouse ears; (b) the TPA-induced oxidative burst by human PMNs and probably also by mouse PMNs; (c) $H_2O_2$ production in TPA-treated mouse skin; and (d) formation of oxidized bases in epidermal DNA isolated from in vivo-treated mouse skin, as determined by the presence of HMdUrd and 8-OHdGua.

At higher doses, CAPE additionally inhibits the following TPA-mediated processes: (a) TPA-induced ear edema in SENCAR mice when the amount of CAPE is 1 µmol/ear and TPA is 0.4 nmol/ear; (b) TPA (5 nmol)-induced ODC in CD-1 mice is inhibited by 55% by 1 μmol CAPE (76), while it takes 10 μmol CAPE to inhibit by 62% the TPA (4 nmol)induced ODC in SENCAR mice; (c) topical application of CAPE (650 nmol/treatment; 2x treatment, 20 h apart) decreased TPA-mediated PMN infiltration and the formation of HMdUrd and 8-OHdGua in SENCAR mice. However, this reduction was not as effective as that caused by the lower (6.5 nmol) dose of CAPE, which was equimolar to that of TPA (Table 3). Only $H_2O_2$ levels were further decreased by the higher dose of CAPE. These results suggest that chemopreventive agents may be very effective at low but not necessarily at high doses. We have noted a similar phenomenon occurring with other protective agents such as EGCG (30). Apparently, higher doses of these substances may interfere with other cellular processes and, in effect, counteract their own protective action.

TABLE 3

CAPE-mediated effects on TPA-induced infiltration
of PMNs, $H_2O_2$ production, and formation of oxidized DNA
bases in skin of SENCAR mice[a]

| Treatment | MPO units/ cm² skin (4)[b] | $H_2O_2$ nmol/cm² skin (5) | HMdUrd/ 10⁴ bases (2) | 8- OHdGua/10⁵ bases (2) |
|---|---|---|---|---|
| Acetone | 0.1 ± 0.03 | 12.8 ± 0.8 | 16.2 ± 7.7 | 5.0 ± 2.0 |
| TPA (6.5 nmol) | 23.7 ± 7.6 | 31.5 ± 0.7 | 39.4 ± 6.4 | 11.8 ± 6.3 |
| TPA/CAPE (6.5 nmol) | 5.9 ± 0.3 | 15.7 ± 2.2 | 13.1 ± 0.6 | 1.4 ± 0.8 |
| TPA/CAPE (650 nmol) | 10.8 ± 2.0 | 11.6 ± 0.6 | 30.5 ± 10.5 | 9.4 ± 1.1 |

[a]Mice were treated as described in the legend to FIG. 2, except that in addition to the group pretreated with 6.5 nmol CAPE, another group was pretreated with 650 nmol CAPE prior to TPA applications. Results are expressed as mean values of 2–5 experiments ± SE. Note that HMdUrd is calculated per 10⁴, while 8-OHdGua is per 10⁵ normal bases.
[b]Numbers in parentheses, number of experiments with CAPE; values for acetone controls or TPA treatments are based on over 20 determinations each.

The very small amounts of CAPE required for protection from oxidative damage indicate that these agents probably act by interfering with the oxidative activation of the cells rather than by being antioxidants, which would require much higher doses needed for scavenging of the reactive oxygen species already produced. That this may be the case is shown by findings that TPA-treated HeLa cells, which were preincubated with low doses (5–25 nmol) of EGCG, contained lower levels of HMdUrd and 8-OHdGua than cells treated only with TPA (30). Similar to what we found for CAPE, higher doses of EGCG (50 nmol) caused a less effective inhibition of TPA-induced oxidative processes.

As we noticed, relatively high doses of CAPE (1–10 μmol) were needed to inhibit 4–5 nmol or 0.4–0.5 nmol of TPA-mediated ODC or edema induction, respectively, in two strains of mice ("Results" Section, Supra, and 76). In contrast, for inhibition of phagocytic infiltration, reactive oxygen species production and oxidative DNA damage in one of those strains (SENCAR), a very low does of CAPE (6.5 nmol)/treatment, 2x treatment, 20 h apart; equimolar to that of TPA) was extremely effective (FIG. 2). PMN infiltration declined by 85%, HMdUrd formation by 115%, and that of 8-OHdGua by near 170%. Both oxidized base derivatives were lowered below the levels present in the acetone-only treated controls, particularly 8-OHdGua, which declined 70% below the basal levels. We previously found that sarcophytol A (an anti-tumor-promoting agent effective in a two-stage carcinogenesis model in mice) at a dose (6.5 nmol) equimolar to that of the tumor promoter (10), was also a potent inhibitor of TPA (6.5 nmol/treatment)-induced oxidative processes (i.e. PMN infiltration, reactive oxygen species generation, and DNA base oxidation) in SENCAR mice (4). That inhibition occurred during the same two-dose treatment that was utilized in the current study, as well as during a typical tumor promotion regimen induced by 3.2 nmol TPA applied twice a week for 16 weeks. Hence, it appears that it is PMN infiltration, reactive oxygen species production, and oxidized DNA base formation that correlate with and might be necessary for tumor promotion, whereas ODC and edema induction alone (without the former three processes) might not be sufficient for tumor promotion. Other investigators, using different experimental designs, also noted dissociation of ODC induction from the requirements for tumor promotion (45, 70).

The other ex vivo system utilized by us also yielded very interesting and potentially important information. TPA-induced $H_2O_2$ production in bovine lenses occurred in a dose-dependent manner, and it caused lens opacification. CAPE suppressed formation of TPA-induced $H_2O_2$ formation and opacification of lenses at a concentration that was 10-fold higher (1 μM) than the TPA (0.1 μM) that induced them. It is suspected that high $Ca^{2+}$ induces lens opacity and causes formation of cataracts (39). Interestingly, it has been found that $H_2O_2$ enhances the activities of $Na^+/Ca^+$ as well as of $Na^+/Ca^+$ exchangers and increases opacity of the bovine lens (31, 68, 69). Hence, it is possible that the $H_2O_2$ produced in response to TPA causes elevation in $Ca^{2+}$ within the lens and, consequently, causes opacity as well. It is encouraging that the chemopreventive agents which suppress oxidative activation of cells also can protect the lens from opacification. Patients with cataracts were shown to have highly elevated levels of $H_2O_2$ (39, 71). $Ca^{2+}$ is also more readily transported into the aging lens, which is more prone to cataract development (72). By enhancing the activity of the $Na^+/H^+$ exchanger, $H_2O_2$ could cause more $Na^{2+}$ accumulation within and less $Na^+$ outside the lens, leading to a higher influx of $Ca^{2+}$ as well as elevation of intracellular pH (68, 69, 73). Similar processes occur during the oxidative burst of PMNs (14) whether caused by TPA or opsonized particulates, with its attendant acidification around the PMN membrane Moreover, $Ca^{2+}$ ionophore also can induce the oxidative burst and activate the NADPH oxidase that is responsible for production of reactive oxygen species (75) as well as cause hydroperoxide production in mouse epidermis in vivo (67).

We also showed that TPA is a potent inducer of cataracts in the eyes of live rabbits and that CAPE injections following the TPA treatments significantly reduced the pathological effects of this phorbol ester.

Thus, two seemingly diverse biological systems may have certain types of responses in common. Tumor promoter-treated mouse skin responds with PMN infiltration and $H_2O_2$ production. Similarly, a TPA-treated lens generates large amounts of $H_2O_2$, which contributes to cataract formation. Both involve change in $Ca^{2+}$ homeostasis, elevation of which can be damaging in both systems. It is of considerable interest that TPA-induced $H_2O_2$ formation as well as opacity of lenses respond to CAPE.

REFERENCES

1. Grunberger, D., Banerjee, R., Eisinger, K., Oltz, E. M., Efros, L., Caldwell, M. Estevez, V., and Nakanishi K. Preferential cytotoxicity on tumor cells by caffeic acid phenethyl ester isolated from propolis. Experientia (Basel), 44: 230–232. 1988

2. Su, Z-Z., Grunberger, D., and Fisher, P. B. Suppression of adenovirus type 5 EIA-mediated transformation and expression of the transformed phenotype by caffeic acid phenethyl ester (CAPE), Mol. Carcinog., 4: 231–242, 1991.
3. Frenkel, K. Carcinogen-mediated oxidant formation and oxidative DNA damage. Phamacol. Ther., 53: 127–166, 1992.
4. Kensler, T. W., and Taffe, B. G. Free radicals in tumor promotion. Adv. Free Radical Biol. Med., 2: 347–387, 1986.
5. D'Onofrio, C., Maly, F. E., Fischer, H., and Maas, D. Differential generation of chemiluminescence detectable oxygen radicals by normal polymorphonuclear leukocytes challenged with sera from systemic lupus erythematosus and rheumatoid arthritis patients. Klin. Wochenschr., 62: 710–716, 1984.
6. Evans, C. R., Omorphos, S. C., and Baysal, E. Sickle cell membranes and oxidative damage. Biochem. J., 237: 265–269, 1986.
7. Frenkel, K., Chrzan, K., Troll, W., Teebor, G. W., and Steinberg, J. J. Radiation-like modification of bases in DNA exposed to tumor promoter-activated PMN leukocytes. Cancer Res., 46: 5533–5540, 1986.
8. Birnboim, H. C. Factors which affect DNA strand breakage in human leukocytes exposed to tumor promoter phorbol myristate acetate. Can. J. Physiol. Pharmacol., 60: 1359–1366, 1982.
9. Cheng, K. C., Cahill, D. S., Kasai, H., Nishimura, S., and Loeb, L. A. 8-Hydroxydeoxyguanosine, an abundant form of oxidative DNA damage causes G-T and A-T substitutions. J. Biol. Chem., 267: 166–172, 1992.
10. Yamamoto, F., Kasai, H., Bessho, T., Chung, M. H., Inoue, H., Obtsuka, E., Hori, T. and Nishimura, S. Ubiquitous presence in mammalian cells of enzymatic activity specifically cleaving 8-hydroxyguanine containing DNA. Jpn. J. Cancer Res., 83: 351–357, 1992.
11. Higgins, S., Frenkel, K., Cummings, A., and Teebor, G. Definitive characterization of human thymine glycol-N-glycosylase activity. Biochemistry, 26: 1683–1688, 1987.
12. Hollstein, M. C., Brooks, P., Linn, S., and Ames, B. Hydroxymethyluracil DNA glycosylase in mammalian cells. Proc. Natl. Acad. Sci. USA, 81: 4003–4007, 1984.
13. Teebor, G. W., Boorstein, R. J. and Cadet, J. The repairability of oxidative free radical-mediated damage to DNA: a review. Int. J. Radiat. Biol., 54: 131–150, 1988.
14. Breimer, L. H. Molecular mechanisms of oxygen radical carcinogenesis and mutagenesis. The role of DNA base damage. Mol. Carcinog., 3: 188–197, 1990.
15. Tchou, J., and Grollman, A. P. Repair of DNA containing the oxidatively-damaged base, 8-oxoguanine. Mutat. Res., 299: 277–287, 1993.
16. Waschke, S., Reefschlager, J., Barwolff, D., and Langen, P. 5-Hydroxymethyl-2'-deoxyuridine, a normal DNA constituent in certain *Bacillus subtilis* phages is cytostatic for mammalian cells. Nature (Lond.), 225: 629–630, 1975.
17. Shirname-More, L., Rossman, T., Troll, W., Teebor, G., and Frenkel, K. Genetic effects of 5-hydroxymethyl-2'-deoxyuridine, a product of ionizing radiation. Mutat. Res., 178: 177–186, 1987.
18. Shigenaga, M. K., Gimeno, C-J., and Ames, B. K. Urinary 8-hydroxy-2'-deoxyguanosine as a biological marker of in vivo oxidative DNA damage. Proc. Natl. Acad. Sci. USA, 86: 9697–9701, 1989.
19. Floyd, R. A. The role of 8-hydroxyguanine in carcinogenesis. Carcinogenesis (Lond.). 11: 1447–1450, 1990.
20. Wei, H. and Frenkel, K. In vivo formation of oxidized bases in tumor promoter-treated mouse skin. Cancer Res. 51: 4443–4449, 1991.
21. Wei, H. and Frenkel, K. Suppression of tumor promoter-induced oxidative events and DNA damage in vivo by sarcophytol A: a possible mechanism of antipromotion. Cancer Res. 52: 2298–2303, 1992.
22. Wei, H., and Frenkel K. Relationship of oxidative events and DNA oxidation in SENCAR mice to in vivo promoting activity of phorbol ester-type tumor promoters. Carcinogenesis (London), 14: 1195–1201, 1993.
23. Smart, R. C., Huang, M-T., Han, Z. T., Kaplan, M. C., Focella, A., and Conney, A. H. Inhibition of 12-0-tetradecanoylphorbol-13-acetate induction of ornithine decarboxylase, DNA synthesis, and tumor promotion in mouse skin by ascorbic acid and ascorbyl palmitate. Cancer Res., 47: 6633–6638, 1987.
24. Huang, M. T., Smart, R. C., Wong, C-Q., and Conney, A. H. Inhibitory effect of curcumin, chlorogenic acid, caffeic acid, and ferulic acid on tumor promotion in mouse skin by 12-0-tetradecanoylphorbol-13-acetate. Cancer Res., 48: 5941–5946, 1988.
25. Huang, M-T., Lysz, T., Ferraro, T., Abidi, T. F., Laskin, J. D., and Conney, A. H. Inhibitory effects of curcumin on in vitro lipoxygenase and cyclooxygenase activities in mouse epidermis. Cancer Res., 52: 813–819, 1991.
26. Agarwal, R., Katiyar, S. K., Zaidi, S. I. A., and Mukhtar, H. Inhibition of skin tumor promoter-caused induction of epidermal ornithine decarboxylase in SENCAR mice by polyphenolic fraction isolated from green tea and its individual epicatechin derivatives, Cancer Res., 52: 3582–3588, 1992.
27. Fujiki, H., H. Suganuma, M., Supuri, H., Yoshizawa, S., Takagi, K., and Kobayashi, M. Sarcophytols A and B inhibit tumor promotion by teleocidin in two-stage carcinogenesis in mouse skin. J. Cancer Res. Clin. Oncol., 115: 25–28, 1989.
28. Frenkel, K., Zhong, Z., Rashid, K., and Fujiki, H. Sarcophytols and protease inhibitors suppress $H_2O_2$ formation and oxidative DNA damage. In: O. F. Nygaard (ed.), Anticarcinogenesis and Radiation Protection, Vol. 2. pp 357–366. New York Plenum Publishing Corp., 1991.
29. Yoshizawa, S., Horiuchi, T., Fujiki, H., Yoshida, T., Okuda, T., and Sugimura, T. Antitumor promoting activity of (−)epigallocatechin gallate, the main constituent of "tannin" in green tea. Phytother. Res., 1: 44–47, 1987.
30. Bhimani, R., Troll, W., Grunberger, D., and Frenkel, K. Inhibition of oxidative stress in HeLa cells by chemopreventive agents Cancer Research, 53: 4528–4533, 1993.
31. Ye, J., Frenkel, K., and Zadunaisky, J. A. Lens opacification and $H_2O_2$ elevation induced by a tumor promoter. Lens Eye Tox. Res., 9: 37–48, 1992.
32. Bhuyan, K., Master, R. W. Coles, R. S., Bhuyan, D. K. Molecular mechanism of cataractogenesis: IV. Evidence of phospholipid malondialdehyde adduct in human senile cataract. Mech. Ageing Dev. 34: 289–296, 1986.
33. Varma, S. D., Chand, D., Sharma, Y. R., Kuck, J. F., Richards, R. D. Oxidative stress on lens and cataract formation: Role of light and oxygen. Curr. Eye Res. 3: 35–57, 1884.
24. Spector, A., Wang, G-M., Wang, R-R. Photochemically induced cataracts in rat lenses can be prevented by AL-3823A, a glutathione peroxidase mimic. Proc. Natl. Acad. Sci. USA. 90: 7485–7489, 1993.
25. Bhuyan, K. C., Bhuyan, D. K. Regulation of hydrogen peroxide in eye tumors. Effect of 3-amino-1H-1, 2, 4-triazole on catalase and glutathione peroxidase of rabbit eye. Biochim. Biophys. Acta. 497: 641–651, 1977.
36. Bhuyan, K. C., Bhuyan, D. K. Superoxide dismutase of the eye: Relative functions of superoxide dismutase and catalase in protecting the ocular lens from oxidative damage. Biochim. Biophys. Acta. 542: 28–38, 1978.

27. Bhuyan, K. C., Bhuyan, D. K., Podos, S. M. Free radical enhancer xenobiotic as an inducer of cataract in rabbit. Free Radic. Res. Comm. 12–13: 609–620, 1991.
28. Goosey, J. D., Zigler, J. S., Kinoshita, J. H. Cross linking of lens crystallins in a photodynamic system: A process mediated by singlet oxygen. Science 208: 1278–1280, 1980.
29. Spector, A. Aspects of the biochemistry of cataracts. The Ocular Lens, Structure, Function and Pathology. New York: Maisel, H, Marcel Dekker Inc: 405–438, 1985.
40. Augusteyn, R. C. Protein modification in cataract: Possible oxidative mechanism. Mechanism of Cataract Formation in the Human Lens. New York: Academic Press. 71–115, 1981.
41. Babizhayev, M. A. Accumulation of lipid proxidation products in human cataracts. Acta Ophthalmol. 67: 281–287, 1989.
42. Bhuyan, K. C., Bhuyan, D. K. Molecular mechanism of cataractogenesis: III. Toxic metabolites of oxygen as initiators of lipid peroxidation and cataract Curr. Eye Res. 13: 67–81, 1984.
43. Bhuyan, K. C., Bhuyan, D. K., Podos, S. M. Lipid peroxidation in cataract of the human. Life Sci. 38: 1463–1471, 1986.
44. Fischer, S. M., Baldwin, J. K., and Adams, L. M. Effects of anti-promoters and strain of mouse on tumor promoter-induced oxidants in murine epidermal cells. Carcinogenesis (Lond.), 7: 915–918, 1986.
45. Perchellet, E. M., and Perchellet, J-P. Characterization of the hydroperoxide response observed in mouse skin treated with tumor promoter in vivo. Cancer Res., 49: 6193–6201, 1989.
46. Kensler, T. W., Egner, P. A. Taffe. B. G., and Trush, M. A. Role of free radicals in tumor promotion and progression. In: T. J. Slaga, A. J. P. Klein-Szanto, R. K. Boutwell, D. E. Stevenson, H. L. Spitzer, and B. D'Motto (eds). Skin Carcinogenesis Mechanisms and Human Relevance, pp. 233–248. New York; Alan R. Liss. Inc., 1989.
47. Perchellet, J-P., and Perchellet, E. M. Antioxidants and multistage carcinogenesis in mouse skin. Free Rad. Bio. Med., 7: 377–108, 1989.
48. Fesen, M. R., Kohn, K. W., Leteurtre, F., and Pommier, Y. Inhibitors of Human Immunodeficiency Virus Integrase. Proc. Natl. Acad. Sci. USA. 90: 2399–2403, 1993.
49. Kasai, H., and Nishimura, S. Hydroxylation of deoxyguanosine at the C-8 position by ascorbic acid and other reducing agents. Nucleic Acids Res., 12: 2137–2145, 1984
50. Frenkel, K., Zhong, Z., Wei, H., Karkoszka, J., Patel, U., Rashid, K., Georgescu, M. and Solomon, J. Quantitative high-performance liquid chromatography analysis of DNA oxidized in vitro and in vivo. Anal. Biochem., 196: 126–136, 1991.
51. Matsuda, T. A., Shinozaki, M., Suzuki, M., Watanabe, K., and Miyasaka, T. Convenient method for the selective acylation of guanine nucleosides. Synthesis, 385–386, 1986.
52. Bradford, M. M. A rapid and sensitive method for the quantitation of microgram quantities of protein utilizing the principle of protein-dye binding. Anal. Biochem., 72: 248–254, 1976.
53. Metcalf. J. A., Gallin, J. I., Nauseef, W. M., and Root, R. K. Laboratory Manual of Neutrophil Function, pp. 150–151. New York: Raven Press, 1986.
54. Frenkel, K., and Chrzan, K. Hydrogen peroxide formation and DNA base modification by tumor promoter-activated polymorphonuclear leukocytes. Carcinogenesis (Lond.). 8: 455–460, 1987.
55. Frenkel, K., and Gleichauf, C. Hydrogen peroxide formation by cells treated with a tumor promoter. Free Rad. Res. Commun., 13: 783–794, 1991.
56. Srimal, R. C., and Dhavan, B. N. Pharmacology of diferuloyl methane (curcumin), a non-steroidal anti-inflammatory agent. J. Pharm. Pharmacol., 25: 447–452, 1973.
57. Sharma, O. P. Antioxidant activity of curcumin and related compounds. Biochem Pharmacol., 25: 1811–1812, 1976.
58. Rao, T. S., Basu, N., and Siddiqui, H. H. Anti-inflammatory activity of curcumin analogues, Indian J. Med. Res., 75: 574–578, 1982.
59. Warren, J. S., Johnson, K. J., and Ward, P. A. Oxygen radicals in cell injury and cell death. Pathol. Immunopatho. Res. 6: 301–315, 1987.
60. Frenkel, K. Oxidation of DNA bases by tumor promoter-activated processes. Environ Health Perspect. 81: 45–54, 1989.
61. Frenkel, K., Chrzan, K., Ryan, C. A. Wiesner, R., and Troll, W. Chymotrypsin specific protease inhibitors decrease $H_2O_2$ formation by activated human polymorphonuclear leukocytes. Carcinogenesis (Lond.), 8: 1207–1212, 1987.
62. Zhong, Z., Tius, M., Troll, W., Fujiki, H., and Frenkel, K. Inhibition of $H_2O_2$ formation by human polymorphonuclear leukocytes (PMNs) as a measure of anticarcinogenic activity Proc. Am. Assoc. Cancer Res., 32: 127, 1991.
63. Lim, J. S., Frenkel, K., and Troll, W. Tamoxifen suppresses tumor promoter-induced hydrogen peroxide formation by human neutrophils. Cancer Res., 52: 4969–4972, 1992.
64. Boynton, A. L., Whitfield, J. F., and Isaaks, R. J. Calcium-dependent stimulation of BALB/c 3T3 mouse cell DNA synthesis by a tumor-promoting phorbol ester (PMA). J. Cell. Physiol., 87: 25–32. 1976.
65. Verma, A. K., and Boutwell, R. K. Intracellular calcium and skin tumor promotion: Calcium regulation of the induction of epidermal ornithine decarboxylase activity by tumor promoter 12-O-tetradecanoylphorbol-13-acetate. Biochem. Biophys. Res. Commun., 101: 375–383, 1981.
66. Wirth, P. J., Yuspa, S. H., Thorgeirsson, S. S., and Hennings, H. Induction of common patterns of polypeptide synthesis and phosphorylation by calcium and 12-O-teradecanoylphorbol-13-acetate in mouse epidermal cell culture. Cancer Res., 47: 2831–2838. 1987.
67. Perchellet, E. M., Jones, D., and Perchellet, J-P. Ability of the $Ca^{2+}$ ionophores A23187 and tenomycin to mimic some of the effects of the tumor promoter 12-O-tetradecanoylphorbol-13-acetate on hydroperoxide production, ornithine decarboxylase activity, and DNA synthesis in mouse epidermis in vivo. Cancer Res., 50: 5806–5812, 1990.
68. Ye. J., and Zadunaisky, J. A. Study of the $Ca^{2+}/Na^+$ exchange mechanism in vesicles isolated from apical membranes of lens epithelium of spiny dogfish (*Squalus acanthias*) and bovine eye. Exp. Eye Res., 55: 243–250, 1992.
69. Ye. J., and Zadunaisky, J. A. A $Na^+/H^+$ exchanger and its relation to oxidative effects of plasma membrane vesicles from lens fibers. Exp. Eye Res., 55: 251–260, 1992.
70. Fischer, S. M., Baldwin, J. K., Jasheway, D. W., Patrick, K. E., and Cameron, G. S. Phorbol ester induction of 8-lipoxygenase in inbred SENCAR (SSIN) but not C57BL/6J mice correlated with hyperplasia, edema, and oxidant generation but not ornithine decarboxylase induction. Cancer Res., 48: 658–664, 1988.

71. Spector, A., and Garner, W. H. Hydrogen peroxide and human cataract. Exp. Eye Res., 33: 673–681, 1981.
72. Duncan, G., Hightower, K. R., Gandolfi, S. A., Tomlinson, J., and Mareini, G. Human lens membrane cation permeability increases with age. Invest. Ophthalmol. Vis. Sci. 30: 1855–1859, 1989.
73. Alvarez, J., Garcia-Sancho, J., Mollinedo, F. and Sanchez, A. Intracellular $Ca^{2+}$ potentiates $Na^+/H^+$ exchange and cell differentiation induced by phorbol ester in U937 cells. Eur. J. Biochem., 183: 709–714, 1989.
74. Araki, A., Inoue, T., Cragoe, E. J., Jr., and Sendo, F. $Na^+/H^+$ exchange modulates rat neutrophil mediated tumor cytotoxicity. Cancer Res., 51: 3212–3216, 1991.
75. Follin, P., Johansson, A., and Dahlgren, C. Intracellular production of reactive oxygen species in human neutrophils following activation by the soluble stimuli FMLP, dioctanoylglycerol and ionomycin. Cell Biochem. Funct., 9: 29–37, 1991.
76. Frenkel, K., Wei, H., Bhimani, R., Ye, J., Zadunaisky, J., Huang, M-T., Ferraro, T., Conney, A. H., and Grunberger, D. Inhibition of tumor promoter-mediated processes in mouse skin and bovine lens by caffeic acid phenethyl ester. Cancer Research, 53: 1255–1261, 1993.

We claim:

1. A method of inhibiting the formation of a cataract in an eye, which comprises contacting the eye with an effective cataract-inhibiting amount of a compound having the structure:

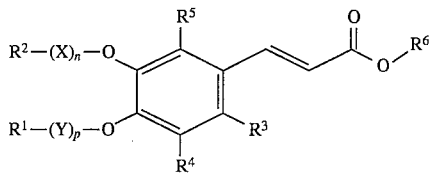

wherein

X and Y are independently carbonyl, C=S, S=O, or O=S=O; n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^8$ are independently $C_1$–$C_6$ linear or branched alkyl;

$R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, including F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

2. The method of claim 1, wherein n and p are 0, and $R_1$, $R_2$, $R_3$, $R_4$, and $R_5$ are hydrogen.

3. The method of claim 2, wherein $R_6$ is hexyl, butyl, ethyl, or phenylethyl.

4. The method of claim 1, wherein the compound has the structure:

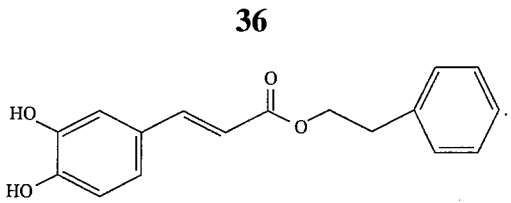

5. The method of claim 1, wherein the eye contains a developing or fully developed cataract.

6. The method of claim 1, wherein the eye does not contain a developing or fully developed cataract.

7. A method of inhibiting the formation of a cataract in an eye of a subject which comprises administering to the subject a pharmaceutical composition which comprises a pharmaceutically acceptable carrier and an effective cataract-inhibiting amount of a compound having the structure:

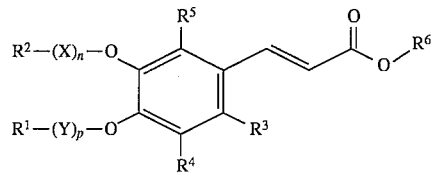

wherein

X and Y are independently carbonyl, C=S, S=O, or O=S=O; n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^8$ are independently $C_1$–$C_6$ linear or branched alkyl;

$R^3$, $R^4$, and $R^5$, are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, including F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

8. The method of claim 7, wherein n and p are 0, and $R_1$, $R_2$, $R_3$, $R_4$, and $R_5$ are hydrogen.

9. The method of claim 8, wherein $R_6$ is hexyl, butyl, ethyl, or phenylethyl.

10. The method of claim 7, wherein the compound has the structure:

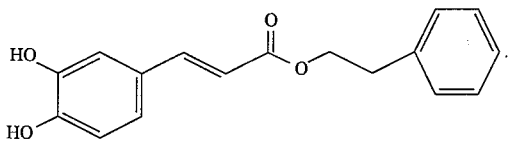

11. The method of claim 7, wherein the eye contains a developing or fully developed cataract.

12. The method of claim 7, wherein the eye does not contain a developing or fully developed cataract.

13. The method of claim 7, wherein the subject is a mammal.

14. The method of claim 13, wherein the subject is a human.

15. The method of claim 7, wherein administering the pharmaceutical composition to the subject comprises applying the pharmaceutical composition to the eye of the subject.

16. A method of inhibiting the progression of cataract formation in an eye which comprises contacting the eye with an effective cataract-inhibiting amount of a compound having the structure:

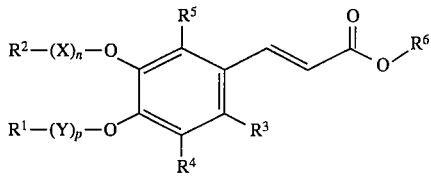

wherein

X and Y are independently carbonyl, C=S, S=O, or O=S=O; n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^8$ are independently $C_1$–$C_6$ linear or branched alkyl;

$R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, including F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

17. The method of claim 16, wherein n and p are 0, and $R_1$, $R_2$, $R_3$, $R_4$, and $R_5$ are hydrogen.

18. The method of claim 17, wherein $R_6$ is hexyl, butyl, ethyl, or phenylethyl.

19. The method of claim 16, wherein the compound has the structure:

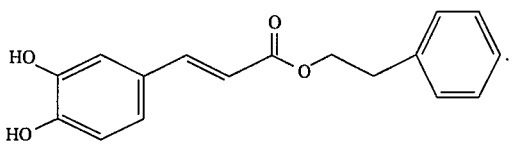

20. The method of claim 16, wherein the eye contains a developing or fully developed cataract.

21. The method of claim 16, wherein the eye does not contain a developing or fully developed cataract.

22. A method of inhibiting the progression of cataract formation in an eye of a subject which comprises administering to the subject a pharmaceutical composition which comprises a pharmaceutically acceptable carrier and an effective cataract-inhibiting amount of a compound having the structure:

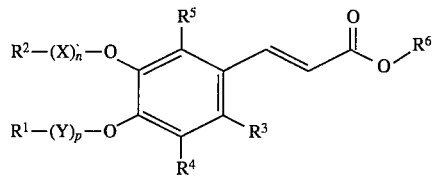

wherein

X and Y are independently carbonyl, C=S, S=O, or O=S=O; n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^8$ are independently $C_1$–$C_6$ linear or branched alkyl;

$R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S)$R^{14}$, (S=O)$R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, including F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

23. The method of claim 22, wherein n and p are 0, and $R_1$, $R_2$, $R_3$, $R_4$, and $R_5$ are hydrogen.

24. The method of claim 23, wherein $R_6$ is hexyl, butyl, ethyl, or phenylethyl.

25. The method of claim 22, wherein the compound has the structure:

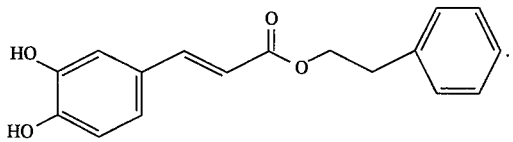

26. The method of claim 22, wherein the eye contains a developing or fully developed cataract.

27. The method of claim 22, wherein the eye does not contain a developing or fully developed cataract.

28. The method of claim 22, wherein the subject is a mammal.

29. The method of claim 28, wherein the subject is a human.

30. The method of claim 22, wherein administering the pharmaceutical composition to the subject comprises applying the pharmaceutical composition to the eye of the subject.

* * * * *